United States Patent
Yamamoto et al.

(10) Patent No.: US 12,420,676 B2
(45) Date of Patent: Sep. 23, 2025

(54) SENSOR-EQUIPPED SEAT

(71) Applicant: Sumitomo Riko Company Limited, Aichi (JP)

(72) Inventors: Hirokazu Yamamoto, Aichi (JP); Koichi Hasegawa, Aichi (JP); Masaru Murayama, Aichi (JP)

(73) Assignee: Sumitomo Riko Company Limited, Aichi (JP)

( * ) Notice: Subject to any disclaimer, the term of this patent is extended or adjusted under 35 U.S.C. 154(b) by 21 days.

(21) Appl. No.: 18/638,625

(22) Filed: Apr. 17, 2024

(65) Prior Publication Data

US 2024/0262256 A1   Aug. 8, 2024

Related U.S. Application Data

(63) Continuation of application No. PCT/JP2022/040439, filed on Oct. 28, 2022.

(30) Foreign Application Priority Data

Mar. 4, 2022 (JP) .................................. 2022-033077

(51) Int. Cl.
*B60N 2/00* (2006.01)
*B60N 2/56* (2006.01)

(52) U.S. Cl.
CPC .............. *B60N 2/002* (2013.01); *B60N 2/56* (2013.01)

(58) Field of Classification Search
CPC .................................. B60N 2/002; B60N 2/56
See application file for complete search history.

(56) References Cited

U.S. PATENT DOCUMENTS 5,895,900 A * 4/1999 Okada ............... B60R 21/01516
  200/86 R
6,490,936 B1 * 12/2002 Fortune .............. G01G 19/4142
  177/144

(Continued)

FOREIGN PATENT DOCUMENTS

JP   6409466   10/2018

OTHER PUBLICATIONS

"International Search Report (Form PCT/ISA/210) of PCT/JP2022/040439", mailed on Jan. 24, 2023, with English translation thereof, pp. 1-4.

*Primary Examiner* — Hoi C Lau
(74) *Attorney, Agent, or Firm* — JCIPRNET

(57) ABSTRACT

A sensor-equipped seat (1) is provided with a seating-surface seat cushion (10) that comprises: a first seating-surface seat cushion (12) having an accommodation recess (80); and a second seating-surface seat cushion (15) which is accommodated within the accommodation recess (80). Disposed between a first pressing surface (82b) of the accommodation recess (80) in the first seating-surface seat cushion (12) and a second pressing surface (15a) of the second seating-surface seat cushion (15) is a flexible sensor (3) that detects seating condition of a seated person or biological information of the seated person. The first seating-surface seat cushion (12) and the second seating-surface seat cushion (15) are pre-compressed in the stacking direction. Pre-compression is applied to the sensor (3) by compressive reactions of the first seating-surface seat cushion (12) and the second seating-surface seat cushion (15).

22 Claims, 14 Drawing Sheets

(56) References Cited

U.S. PATENT DOCUMENTS

| | | | |
|---|---|---|---|
| 7,365,278 B2* | 4/2008 | Sallam | B60R 21/01516 200/85 A |
| 7,402,769 B2* | 7/2008 | Sallam | B60R 21/01516 200/85 A |
| 7,405,370 B2* | 7/2008 | Sallam | B60N 2/003 200/85 A |
| 7,428,942 B2* | 9/2008 | Sallam | G01G 19/4142 180/274 |
| 7,518,073 B2* | 4/2009 | Sallam | G01G 19/4142 200/85 A |
| 7,661,764 B2* | 2/2010 | Ali | B60N 2/986 297/452.26 |
| 7,708,341 B2* | 5/2010 | Takai | B60N 2/0027 297/217.3 |
| 7,860,625 B2* | 12/2010 | Jaramillo | G01B 11/16 356/614 |
| 7,890,234 B1* | 2/2011 | Jaramillo | B60R 21/01516 356/614 |
| 9,333,878 B2* | 5/2016 | Goedert | B60N 2/7094 |
| 9,421,884 B2* | 8/2016 | Boyer | B60N 2/0031 |
| 9,630,525 B2* | 4/2017 | Nakazaki | B60N 2/0032 |
| 9,937,838 B2* | 4/2018 | Ito | A47C 7/18 |
| 10,117,589 B2* | 11/2018 | Sugiyama | B60N 2/5891 |
| 10,220,756 B2* | 3/2019 | Onuma | A61H 23/04 |
| 10,486,551 B2* | 11/2019 | Nakazaki | H01H 13/16 |
| 10,486,571 B2* | 11/2019 | Sugiyama | A47C 1/12 |
| 11,046,224 B2* | 6/2021 | Nagasawa | B60N 2/914 |
| 11,465,540 B2* | 10/2022 | Sugiyama | A47C 7/744 |
| 11,498,456 B2* | 11/2022 | Ozawa | B60N 2/003 |
| 11,642,983 B2* | 5/2023 | Ozawa | B60N 2/5825 297/180.12 |
| 11,731,533 B2* | 8/2023 | Ozawa | B60N 2/003 297/217.2 |
| 12,005,812 B2* | 6/2024 | Ozawa | B60N 2/5621 |
| 12,240,366 B2* | 3/2025 | Sugiyama | A47C 7/14 |
| 2005/0093350 A1* | 5/2005 | Ali | B60R 21/01516 297/217.3 |
| 2006/0086595 A1* | 4/2006 | Sallam | B60R 21/01516 200/85 A |
| 2006/0091656 A1* | 5/2006 | Sallam | B60R 21/01516 280/735 |
| 2006/0091657 A1* | 5/2006 | Sallam | B60N 2/003 280/735 |
| 2006/0097497 A1* | 5/2006 | Sallam | G01G 19/4142 280/735 |
| 2007/0267282 A1* | 11/2007 | Sallam | B60N 2/003 200/85 A |
| 2008/0191524 A1* | 8/2008 | Takai | B60N 2/686 297/217.2 |
| 2009/0143943 A1* | 6/2009 | Jaramillo | B60N 2/0025 297/217.3 |
| 2011/0029204 A1* | 2/2011 | Jaramillo | B60N 2/267 701/45 |
| 2015/0123436 A1* | 5/2015 | Boyer | B60N 2/0031 297/217.2 |
| 2015/0143927 A1* | 5/2015 | Goedert | B60R 21/01516 73/862.641 |
| 2016/0152168 A1* | 6/2016 | Ito | A47G 9/10 297/452.48 |
| 2016/0214505 A1* | 7/2016 | Nakazaki | H01H 3/14 |
| 2016/0317047 A1* | 11/2016 | Sugiyama | B60N 2/643 |
| 2017/0369018 A1* | 12/2017 | Hüther | B60N 2/0025 |
| 2018/0000422 A1* | 1/2018 | Mitani | A61B 5/0205 |
| 2018/0072186 A1* | 3/2018 | Nakazaki | H01H 13/16 |
| 2018/0086238 A1* | 3/2018 | Onuma | B60N 2/976 |
| 2018/0118071 A1* | 5/2018 | Sugiyama | A47C 7/744 |
| 2020/0101882 A1* | 4/2020 | Sugiyama | A47C 7/14 |
| 2020/0307414 A1* | 10/2020 | Ozawa | B60N 2/003 |
| 2020/0307433 A1* | 10/2020 | Nagasawa | B60N 2/914 |
| 2020/0346570 A1* | 11/2020 | Sugiyama | A47C 7/62 |
| 2021/0138942 A1* | 5/2021 | Kim | B60N 2/5657 |
| 2021/0323443 A1* | 10/2021 | Ozawa | B60N 2/5685 |
| 2022/0194264 A1* | 6/2022 | Kaku | B60N 2/002 |
| 2023/0066789 A1* | 3/2023 | Sugiyama | A47C 7/744 |
| 2023/0226955 A1* | 7/2023 | Ozawa | B60N 2/0034 |
| 2024/0083317 A1* | 3/2024 | Sugiyama | A47C 9/02 |
| 2024/0262256 A1* | 8/2024 | Yamamoto | B60N 2/002 |
| 2024/0270123 A1* | 8/2024 | Hasegawa | A61B 5/1116 |
| 2024/0294096 A1* | 9/2024 | Ozawa | B60N 2/5621 |
| 2024/0391372 A1* | 11/2024 | Tanaka | B60N 2/0264 |
| 2024/0396122 A1* | 11/2024 | Tanabe | B60N 2/16 |
| 2024/0399937 A1* | 12/2024 | Tanabe | B60N 2/64 |
| 2025/0170939 A1* | 5/2025 | Sugiyama | B60N 2/90 |

\* cited by examiner

SENSOR-EQUIPPED SEAT

CROSS-REFERENCE TO RELATED APPLICATION

This application is a continuation of PCT International Application No. PCT/JP2022/040439, filed on Oct. 28, 2022, which claims priority under 35 U.S.C § 119(a) to Japanese Patent Application No. 2022-033077, filed on Mar. 4, 2022. Each of the above application(s) is hereby expressly incorporated by reference, in its entirety, into the present application.

BACKGROUND

Technical Field

The disclosure relates to a sensor-equipped seat.

Description of Related Art

Patent Document 1 discloses a configuration in which a sensor is disposed in a seat, and a seated state (seated posture, etc.) of a seated person or biological information (breathing, pulses, heartbeats, etc.) of the seated person is obtained. In Patent Document 1, the sensor is disposed to be sandwiched between a seat frame and a seat cushion in a state of being installed to the seat frame. The sensor, for example, detects a body surface displacement that occurs together with a pulse or breathing of the seated person by irradiating electromagnetic waves upward (the seated person that is seated) at a predetermined irradiation angle with respect to the horizontal direction and receiving and detecting reflected waves thereof.

PRIOR ART DOCUMENT(S)

Patent Document(s)

[Patent Document 1: Japanese Patent No. 6409466

For example, as a sensor, the use of a pressure sensor that detects a pressure applied to the seat when the seated person is seated is considered.

However, in the case where the pressure sensor is disposed at the seat frame, there is an issue that as the distance between the buttocks of the seated person and the sensor is large, the strength of the biological signal of the seated person decreases.

Besides, in the case where the sensor is disposed at the frame, there is an issue that the vibration noise from the vehicle is directly transmitted to the sensor.

The disclosure provides a sensor-equipped seat in which the strength of a biological signal that is detected is increased, and the noise is decreased.

SUMMARY

An aspect of the disclosure provides a sensor-equipped seat. The sensor-equipped seat includes: an installation member, having an installation seating surface; a seat cushion, which is a seat cushion installed to the installation seating surface of the installation member and has: a first cushion having an accommodation concave part open to a side of the installation member in a counter pressure-receiving surface located on a back side of a pressure-receiving surface receiving a pressure from a seated person; and a second cushion, accommodated in the accommodation concave part of the first cushion to be stacked on the first cushion; and a sensor, disposed between a first pressing surface located on a side opposite to a direction in which the accommodation concave part is open in the accommodation concave part of the first cushion and a second pressing surface located on a side opposite to the installation member in the second cushion, detecting a seated state of the seated person or biological information of the seated person by detecting a physical quantity in accordance with a pressure transmitted from the pressure-receiving surface of the seat cushion via the first cushion in the seated state by the seated person, and having a flexible property. The seat cushion is installed to the installation seating surface of the installation member and, in an unseated state prior to the seated person being seated at the seat cushion, the first cushion and the second cushion are pre-compressed in a stacking direction in which the first cushion and the second cushion are stacked, and the sensor is applied with pre-compression by a compression reaction force of the first cushion and the second cushion.

BRIEF DESCRIPTION OF THE DRAWINGS

The sensor is accommodated in the accommodation concave part provided in the first cushion. Therefore, compared with the case of being installed to the installation member, the sensor is disposed at a position close to the pressure-receiving surface of the first cushion. Accordingly, the attenuation of the biological signal transmitted from the seated person due to the first cushion is suppressed. Consequently, the strength of the biological signal received by the sensor can be increased.

Moreover, since the second cushion is interposed between the sensor and the installation member, the vibration noise from the vehicle can be attenuated by the second cushion.

Since the sensor is flexible, when the seat cushion is deformed with the seated person being seated at the seat cushion, the sensor also deforms in accordance with the deformation of the seat cushion. Accordingly, the noise differing from the pressure from the seated person can be suppressed.

In addition, since the pre-compression due to the compression reaction force of the first cushion and the second cushion is applied to the sensor, when the seated person is seated at the seat cushion, even if the force applied from the seated person to the seat cushion is small, the force can be transmitted to the sensor. As a result, the sensitivity of the sensor can be increased.

According to the above, in the sensor-equipped seat, the strength of the biological signal that is detected is increased, and the noise is decreased.

The symbols in the parentheses indicated in the claimed scope suggest the correspondence with specific means described in the embodiments described in the following and shall not be construed as limitations on the technical scope of the disclosure.

Embodiment 1

1-1. Overall Configuration of the Sensor-Equipped Seat 1

The overall configuration of a sensor-equipped seat 1 is described with reference to FIG. 1. The sensor-equipped seat 1, for example, is applicable to a vehicle seat for an automobile or a railway vehicle, etc., or a medical examination seat, etc. The sensor-equipped seat 1 is used to detect a seated state of a seated person or biological information of the seated person. The seated state of the seated person as the detection target includes, for example, a seated posture, a change of the seated posture, etc. The biological information of the seated person as the detection target includes breathing, pulses, heartbeats, etc., of the seated person.

For example, in the case where the sensor-equipped seat 1 is applied to a driver's seat among seats for a vehicle, the sensor-equipped seat 1 is used to detect the seated state of the driver or the biological information of the driver at the time of driving.

Figure 1:
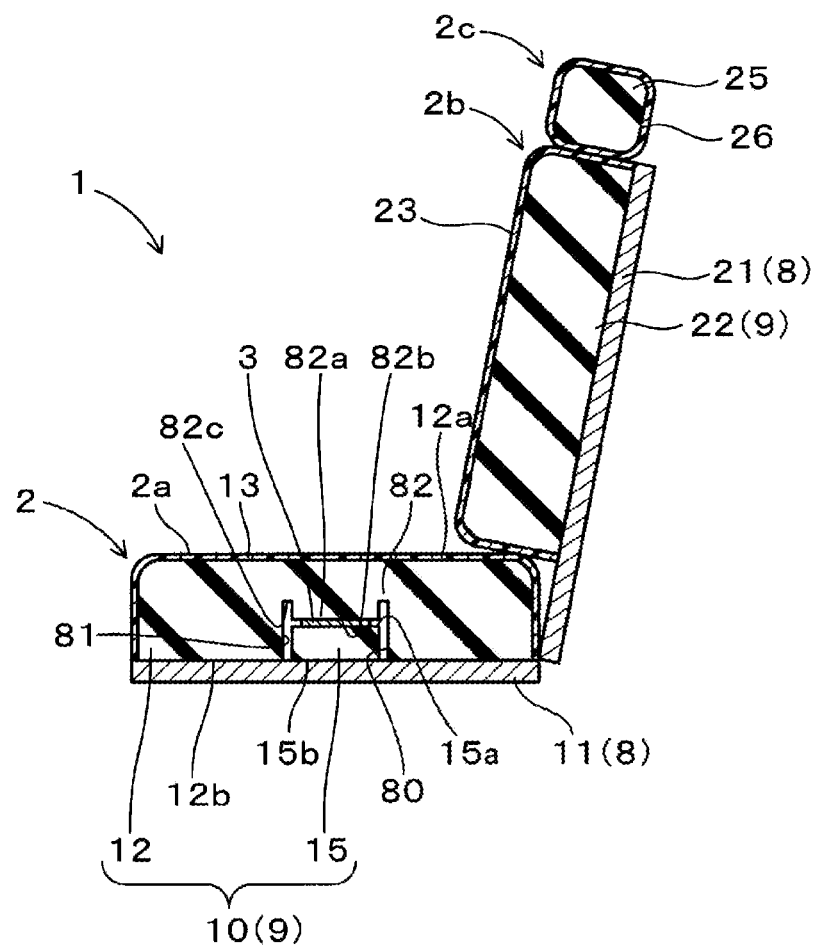
FIG. 1 is a cross-sectional view illustrating a sensor-equipped seat according to Embodiment 1.

The sensor-equipped seat 1 includes a frame part 8, a cushion part 9, and a sensor 3, as shown in FIG. 1. The sensor-equipped seat 1 of the embodiment includes a head rest 2c. However, the head rest 2c may also be omitted.

The frame 8 includes a seating surface seat frame 11 (an example of an installation part) and a back surface seat frame 21. The cushion part 9 includes a seating surface seat cushion 10 (an example of a seat cushion) installed to the seating surface seat frame 11 and a back surface seat cushion 22 installed to the back surface seat frame 21. The seating surface seat cushion 10 includes a first seating surface seat cushion 12 (an example of first cushion) and a second seating surface seat cushion 15 (an example of second cushion).

The seating surface seat frame 11, for example, is formed by a rigid material, such as metal or hard resin, and is installed to the vehicle. The seating surface seat frame 11 has a plate-shaped part having a plate shape. The plate-shaped part is installed to the vehicle so that the plate surface is oriented in the upper-lower direction. The upper surface of the plate-shaped part is arranged as an installation seating surface 11a to which the first seating surface seat cushion 11 is installed. A portion different from the plate-shaped part in the seating surface seat frame 11 is formed in an arbitrary shape, such as a rod shape, a column shape, etc.

The first seating surface seat cushion 12 is formed by an elastic material, such as a foam resin. The first seating surface seat cushion 12 is installed in a state of being placed on the installation seating surface 11a formed on the upper surface of the seating surface seat frame 11. The upper surface of the first seating surface seat cushion 12 serves as a surface (pressure-receiving surface) 12a receiving the pressure exerted by the buttocks of the seated person. The lower surface of the first seating surface seat cushion 12, that is, a counter pressure-receiving surface 12b, which is a surface on the back side of the pressure-receiving surface 12a, faces the installation seating surface 11a of the seating surface seat frame 11.

The first seating surface seat cushion 12 has an accommodation concave part 80 that opens downward toward the side of the seating surface seat frame 11 on the counter pressure-receiving surface 12b. The cross-sectional shape of the accommodation concave part 80 can be arranged in an arbitrary shape, such as a polygonal shape, a circular shape, an elongated circular shape. The cross-sectional shape of the accommodation concave part 80 of the embodiment is arranged in a rectangular shape. In the accommodation concave part 80, a portion located on a side opposite to the direction in which the accommodation concave part 80 is open is arranged as a bottom part 82 of the accommodation concave part 80.

In the accommodation concave part 80, the second seating surface seat cushion 15 is accommodated. The second seating surface seat cushion 15 is installed to the installation seating surface 11a of the seating surface seat frame 11. In the second seating surface seat cushion 15, a surface facing the installation seating surface 11a of the seating surface seat frame 11 is arranged as an installation surface 15b. In the state in which the first seating surface seat cushion 12 and the second seating surface seat cushion 15 are installed to the seating surface seat frame 11, the counter pressure-receiving surface 12b of the first seating surface seat cushion 12 and the installation surface 15b of the second seating surface seat cushion 15 are flush. In addition, in the state in which the first seating surface seat cushion 12 and the second seating surface seat cushion 15 are installed to the seating surface seat frame 11, a gap is formed between the inner side surface of the accommodation concave part 80 and the outer side surface of the second seating surface seat cushion 15. The upper surface of the second seating surface seat cushion 15 (the surface located on the side opposite to the seating surface seat frame) is arranged as a second pressing surface 15a that presses the sensor 3 from the lower side.

A seating surface skin member 13 (an example of the skin) is stacked on a front surface of the first seating surface seat cushion 12. The seating surface skin member 13 covers at least the pressure-receiving surface 12a of the first seating surface seat cushion 12. The seating surface skin member 13 is formed of a material that is less contractible than the first seating surface seat cushion 12, such as clothes, leather, etc.

The back surface seat frame 21 is, for example, formed by a rigid material, such as metal or hard resin, etc. The back surface seat frame 21 is formed in a plate shape, a rod shape, etc. For example, in the case where a reclining function is provided in a seat body 2, the back surface seat frame 21 is swingably supported by the seating surface seat frame 11. It goes without saying that the seating surface seat frame 21 may also be integrally fixed to the seating surface seat frame 11.

The back surface seat cushion 22 is formed by an elastic material, such as a foam resin. The back surface seat cushion 22 is stacked on and installed to the front surface of the back surface seat frame 21. The front surface of the back surface seat cushion 22 serves as a surface (pressure-receiving surface) that receives a pressure from the back part of the seated person. That is, the counter pressure-receiving surface, which is the rear surface of the back surface seat cushion 22 faces the back surface seat frame 21.

On the front surface of the back surface seat cushion 22, a back surface skin member 23 is stacked. The back surface skin member 23 is covered by the back surface seat cushion 22. The back surface skin member 23 covers at least the pressure-receiving surface of the back surface seat cushion 22. The back surface skin member 23 is formed by a material such as clothes, leather, etc.

The head rest 2c is disposed at the upper end of a seat back surface part 2b. The head rest 2c includes the cushion 25 and a skin member 26. Although the first seating surface seat cushion 12 and the back surface seat cushion 22 are separate components in FIG. 1, the first seating surface seat cushion 12 and the back surface seat cushion 22 may also be integral. In addition, although the back surface seat cushion 22 and the head rest 2c are separate components, the back surface seat cushion 22 and the head rest 2c may also be integral.

The sensor 3 is disposed between a first pressing surface 82b formed in the accommodation concave part 80 of the first seating surface seat cushion 12 and the second pressing surface 15a of the second seating surface seat cushion 15. The first pressing surface 82b is provided at a convex part 82a to be described afterwards. Here, with the seated person being seated at the seat body 2, a pressure is applied from the buttocks of the seated person to the pressure-receiving surface 12a of the first seating surface seat cushion 12, and the pressure is transmitted to the first pressing surface 82b of the first seating surface seat cushion 12 via the first seating surface seat cushion 12. In addition, the sensor 3 receives the pressure from the first pressing surface 82b of the first seating surface seat cushion 12. That is, in the seated state according to the seated person, the sensor 3 detects a physical quantity in accordance with the pressure transmitted from the pressure-receiving surface 12a of the first seating surface seat cushion 12 via the first seating surface seat cushion 12. In addition, based on the detected physical quantity, the sensor 3 detects the seated state of the seated person or the biological information of the seated person.

Although the sensor 3 is disposed at a seat seating surface part 2a, the sensor 3 may also be disposed at the seat back surface part 2b. In this case, the sensor 3 is disposed between the back surface seat frame 21 and the back surface seat cushion 22. In addition, in the seated state according to the seated person, the sensor 3 detects a physical quantity in accordance with the pressure transmitted from the pressure-receiving surface 12a of the back surface seat cushion 22 via the back surface seat cushion 22. In addition, based on the detected physical quantity, the sensor 3 can detect the seated state of the seated person or the biological information of the seated person.

1-2. Configuration of the Sensor 3

Figure 2:
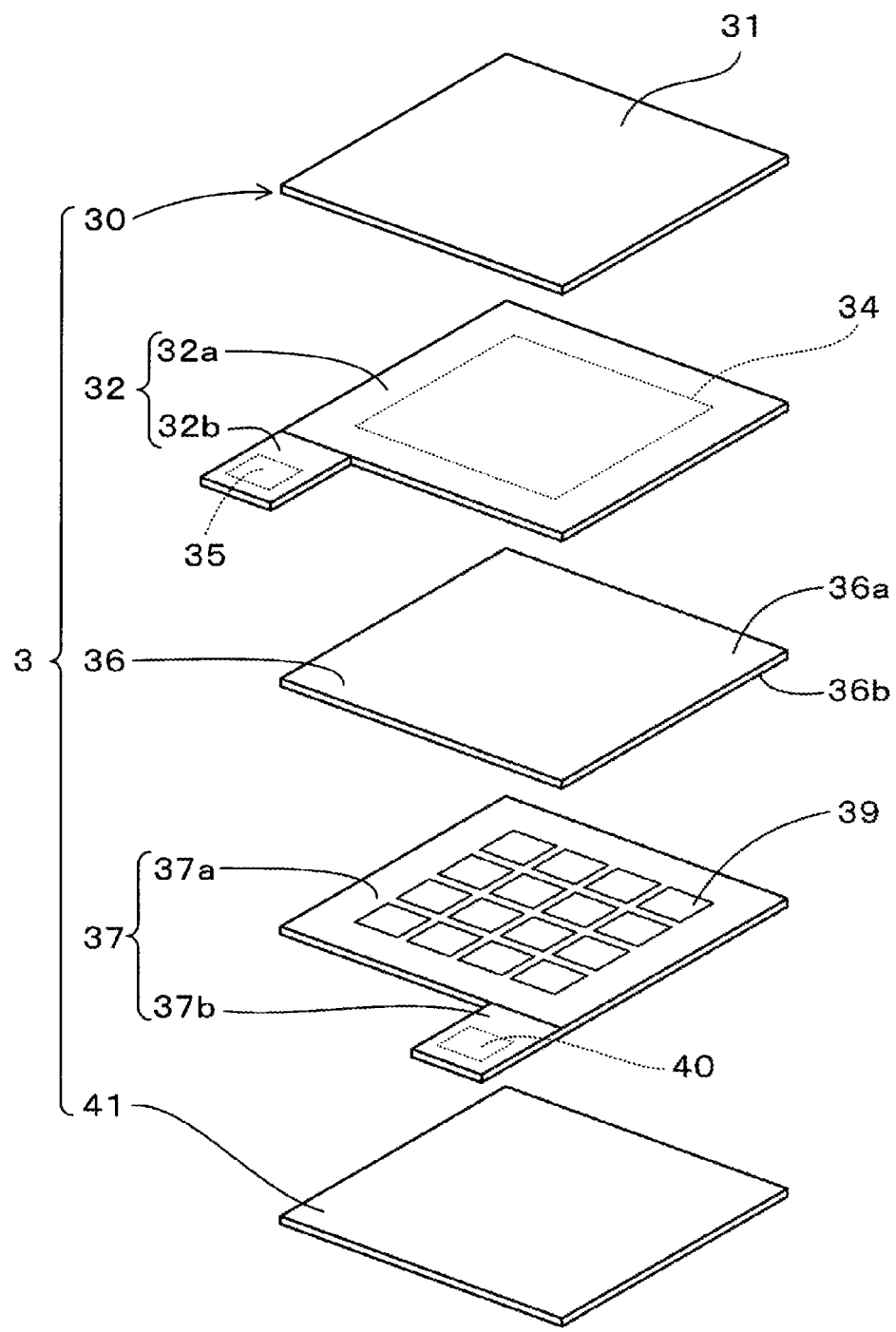
FIG. 2 is an exploded perspective view illustrating a sensor forming the sensor-equipped seat according to Embodiment 1.
Figure 3:
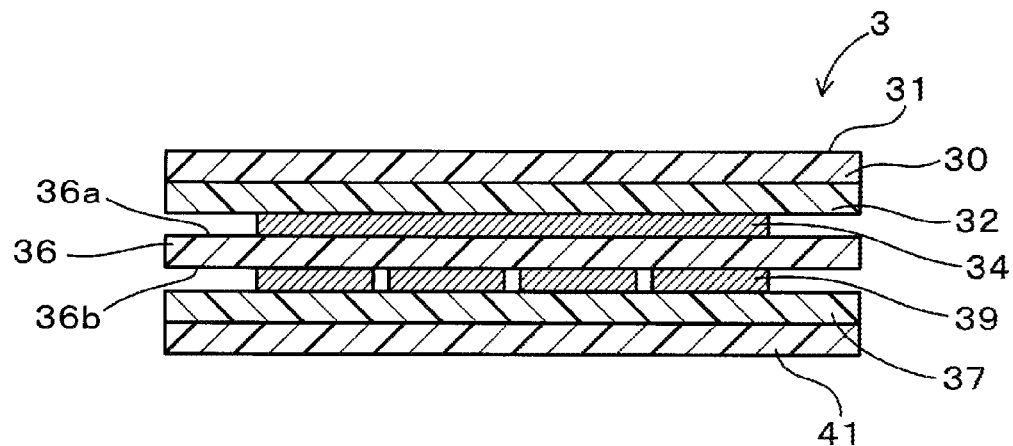
FIG. 3 is a cross-sectional view of the sensor of Embodiment 1.

The configuration of the sensor 3 is described with reference to FIGS. 2 and 3. FIGS. 2 and 3 illustrate the sensor 3 alone, that is, the sensor 3 before being installed to the seat body 2.

The sensor 3 is formed in a flat sheet shape and has a flexible property. The sensor 3 includes an insulator sheet 36, a first electrode sheet 32, a first film sheet 30, a second electrode sheet 37, and a second film sheet 41. The insulator sheet 36 has a first surface 36a and a second surface 36b. The first electrode sheet 32 is stacked on the first surface 36a of the insulator sheet 36. The first film sheet 30 covers the first electrode sheet 32. The second electrode sheet 37 is stacked on the second surface 36b of the insulator sheet 36. The second film sheet 41 covers the second electrode sheet 37. In the following, unless otherwise specified, the stacking direction refers to the stacking direction of the first film sheet 30, the first electrode sheet 32, the insulator sheet 36, the second electrode sheet 37, and the second filter sheet 41 that form the sensor 3.

The insulator sheet 36 is formed in a sheet shape (membrane shape) and has an insulation property as well as a flexible property. The insulator sheet 36, for example, is formed in a rectangular shape. The material forming the insulator sheet 36 is not particularly limited, and may also be formed by a resin or elastomer. As the resin, examples may include polyolefin-based resins and polyamide-based resins. As the elastomer, examples may include urethane-based elastomers, acrylic-based elastomers, ester-based elastomers, polyamide-based elastomers, olefin-based elastomers, and styrene-based elastomers. In the case where the insulator sheet 36 is manufactured by using an elastomer, the insulator sheet 36 is elastically deformable.

The first electrode sheet 32 has a flexible property and is formed in a sheet shape (membrane shape). The first electrode sheet 32, for example, includes a first body part 32a having a rectangular shape, and a first ear part 32b extending from a side of the rectangular shape to a position. The first electrode sheet 32 includes a first electrode layer 34 disposed on a surface (the lower surface of FIG. 2) facing the first surface 36*a* of the insulator sheet 36. The first electrode layer 34 is formed by one of a pair of electrodes arranged on the first surface 36*a* and the second surface 36*b* of the insulator sheet 36, respectively. In the embodiment, the first electrode layer 34 is formed by one electrode. The first ear part 32*b* is electrically connected with the first electrode layer 34, and a first terminal part 35 electrically connected with an external circuit is provided at the first ear part 32*b*.

The first film sheet 30 has an insulation property and a flexible property, and is formed in a sheet shape (membrane shape). The first film sheet 30 is formed by a conventional resin or elastomer. The first film sheet 30 is formed in a rectangular shape, for example. The first film sheet 30 covers a surface on a side opposite to the insulator sheet 36 in the first electrode sheet 32. Accordingly, the first electrode sheet 32 is protected when a stress is applied to the first electrode sheet 32. As a material forming the first film sheet 30, the material may be the same or different from the material forming the insulator sheet 36. In the case where the material forming the first film sheet 30 is a rigid material, the first electrode sheet 32 can be protected. In the first film sheet 30, the surface on a side opposite to the first electrode sheet 32 is arranged as a pressure detection surface 31 that receives a pressure from the first seating surface seat cushion 12.

The second electrode sheet 37 is formed as a separate component from the first electrode sheet 32, and is disposed to face the back surface of the first electrode sheet 32. The second electrode sheet 37, for example, includes a second body part 37*a* having a rectangular shape, and a second ear part 37*b* extending from a side of the rectangular shape. The insulator sheet 36 is interposed between the second electrode sheet 37 and the first electrode sheet 32. The second electrode sheet 37 has a flexible property and is formed in a sheet shape (membrane shape). The second electrode sheet 37 includes a second electrode layer 39 disposed on a surface (the upper surface of FIG. 2) facing the second surface 36*b* of the insulator sheet 36. The second electrode layer 39 is disposed to be spaced apart at a distance and face the first electrode layer 34 forming the first electrode sheet 32. That is, the first electrode layer 34 and the second electrode layer 39 are disposed to be overlapped when projected in the stacking direction. The second electrode layer 39 forms the other of the pair of electrodes for an electrostatic sensor or a piezoelectric sensor.

In addition, in the embodiment, the second electrode layer 39 is formed by multiple electrode groups, and each of the electrodes forming the electrode groups is arranged in a layer direction so as to face one first electrode layer 34 forming the first electrode sheet 32. In the embodiment, as shown in FIG. 2, for example, the second electrode layer 39 is formed by 16 electrodes arranged into four columns and four rows. However, the number of the second electrode group forming the second electrode layer 39 can be set arbitrarily. In addition, the second electrode sheet 37 includes a print pattern in addition to the second electrode layer 39. The second ear part 37*b* is electrically connected with the second electrode layer 39, and a second terminal part 40 electrically connected with an external circuit is provided at the second ear part 37*b*.

The second film sheet 41 has an insulation property and a flexible property, and is formed in a sheet shape (membrane shape). The second film sheet 41 is formed by resin or elastomer. The second film sheet 41 is formed in a rectangular shape, for example. The second film sheet 41 covers a surface on a side opposite to the insulator sheet 36 in the second electrode sheet 37. Accordingly, the second electrode sheet 37 is protected when a stress is applied to the second electrode sheet 37. As a material forming the second film sheet 41, the material may be the same or different from the material forming the insulator sheet 36. In the case where the material forming the second film sheet 41 is a rigid material, the second electrode sheet 37 can be protected.

The first electrode layer 34 and the second electrode layer 39 may also be each formed by one electrode. In addition, the first electrode layer 34 and the second electrode layer 39 may also be each formed by multiple electrodes. For example, it may be configured that the facing positions of the electrodes forming the first electrode layer 34 and the electrodes facing the second electrode layer 39 are arranged in one row, or arranged in one matrix.

1-3. Configurations of the First Seating Surface Seat Cushion 12 and the Second Seating Surface Seat Cushion 15

Figure 4:
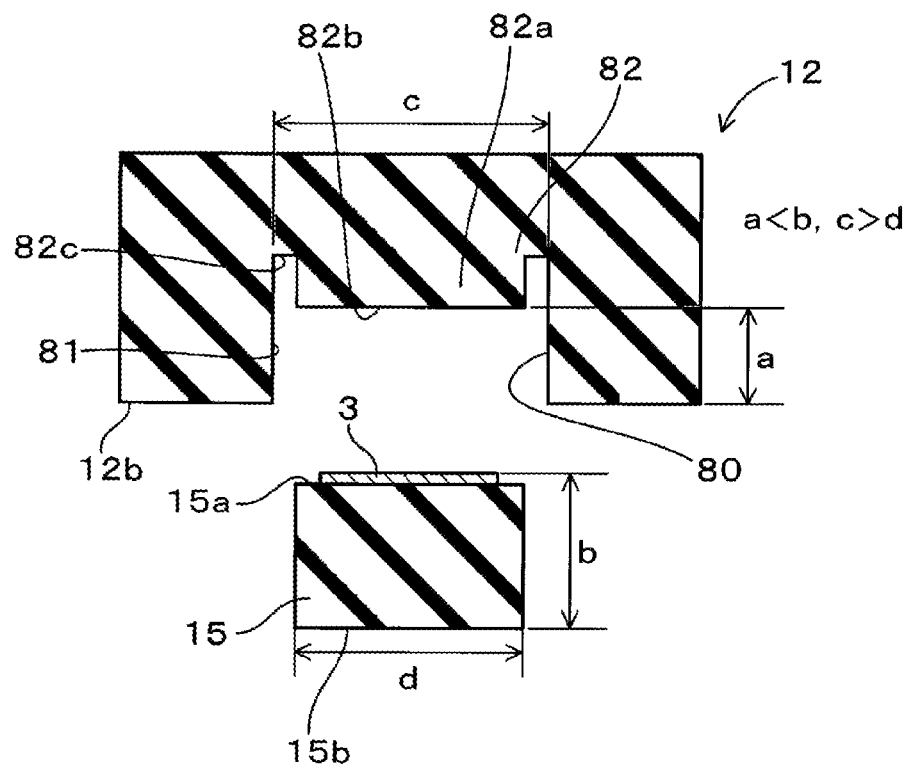
FIG. 4 is a partial cross-sectional view illustrating a state before a first seating surface seat cushion and a second seating surface seat cushion of Embodiment 1 are installed.
Figure 5:
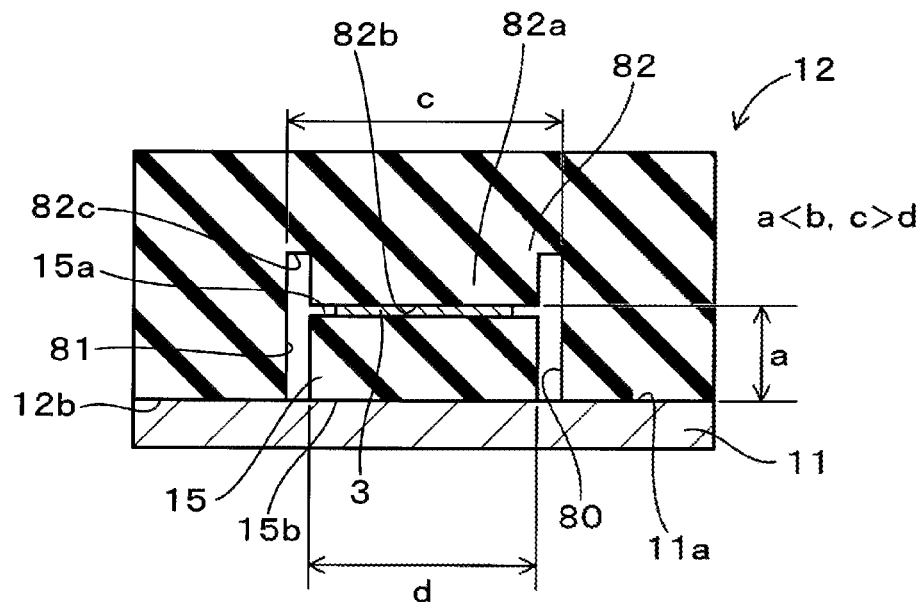
FIG. 5 is a partial cross-sectional view illustrating a state in which the first seating surface seat cushion and the second seating surface seat cushion of Embodiment 1 are installed and further installed to a seating surface seat frame.

The configurations of the first seating surface seat cushion 12 and the second seating surface seat cushion 15 are described with reference to FIGS. 4 and 5. FIG. 4 illustrates the state before the sensor 3 and the second seating surface seat cushion 15 are installed to the first seating surface seat cushion 12. FIG. 5 illustrates the state after the sensor 3 and the second seating surface seat cushion 15 are installed to the first seating surface seat cushion 12.

The first seating surface seat cushion 12 includes the accommodation concave part 80 formed on the counter pressure-receiving surface 12*b*. The accommodation concave part 80 is open to the side opposite to the pressure-receiving surface 12*a* of the first seating surface seat cushion 12, that is, the side of the seating surface seat frame 11. The accommodation concave part 80 accommodates the sensor 3.

The shape of the opening part of the accommodation concave part 80 is formed to be larger than the outer shape of the sensor 3. Although the shape of the opening part of the accommodation concave part 80 is not limited, for example, the opening part of the accommodation concave part 80 is formed in a rectangular shape larger than the outer shape of the sensor 3. In addition, an inner peripheral wall 81 of the accommodation concave part 80 is also formed in a rectangular shape. The inner peripheral wall 81 corresponds to the shape of the outer peripheral surface of the sensor 3 and is formed to be larger than the outer shape of the sensor 3.

The bottom part 82 of the accommodation concave part 80, and has the convex part 82*a* and a recessed groove 82*c*. The convex part 82*a* is formed in the vicinity of the center of the bottom part 82. The convex part 82*a* protrudes from the bottom part 82 of the accommodation concave part 80 toward the opening of the accommodation concave part 80. That is, the convex part 82*a* protrudes from the bottom part 82 toward the side of the seating surface seat frame 11. In addition, a gap is formed between the outer side surface of the convex part 82*a* and the inner side surface of the accommodation concave part 80.

In the embodiment, the convex part 82*a* is formed by an elastic material having a single elastic modulus. The convex part 82*a* is formed by the elastic material forming the first seating surface seat cushion 12. That is, the elastic modulus of the convex part 82*a* is equal to the elastic modulus of other portions forming the first seating surface seat cushion 12.

The recessed groove 82*c* is formed along the edge of the convex part 82*a*. That is, the recessed groove 82*c* forms a boundary portion between the inner side surface and the convex part 82a of the accommodation concave part 80, and is formed throughout the entire edge of the convex part 82a.

The second seating surface seat cushion 15 is formed in a rectangular parallelepiped shape as a whole. The second seating surface seat cushion 15 has the installation surface 15b installed to the seating surface seat frame 11 and the second pressing surface 15a located on a side opposite to the installation surface 15b. The sensor 3 is fixed in a state of being stacked to the second pressing surface 15a. The sensor 3 is fixed to the second pressing surface 15a through a conventional means, such as adhesion, heat fusion.

The first seating surface seat cushion 12 and the second seating surface seat cushion 15 are stacked along the stacking direction defined for the sensor 3.

The second seating surface seat cushion 15 may be formed by the same or different materials as the first seating surface seat cushion 12. In addition, the elastic modulus of the second seating surface seat cushion 15 may be the same as or different from the elastic modulus of the first seating surface seat cushion 12. As will be described in the following, by setting the elastic modulus of the second seating surface seat cushion 15 to be different from the elastic modulus of the first seating surface seat cushion 12, the pressure applied to the sensor 3 can be adjusted.

As a means for setting the elastic modulus of the first seating surface seat cushion 12 and the elastic modulus of the second seating surface seat cushion 15 to be different, for example, the material forming the first seating surface seat cushion 12 and the material forming the second seating surface seat cushion 15 may be different, and the porosity of the first seating surface seat cushion 12 and the porosity of the second seating surface seat cushion 15 may be different. In addition, regarding fillers added to the first seating surface seat cushion 12 and the second seating surface seat cushion 15, the filler type, the filler addition amount, etc., may be different for each of the first seating surface set cushion 12 and the second seating surface seat cushion 15. As described above, the elastic modulus of the first seating surface seat cushion 12 and the elastic modulus of the second seating surface seat cushion 15 can be arranged to be different by an arbitrary means.

In the state in which the second seating surface seat cushion 15 is accommodated in the accommodation concave part 80, the sensor 3 is in a state of being sandwiched between the first pressing surface 82b of the convex part 82a and the second pressing surface 15a of the second seating surface seat cushion 15. In the state in which the second seating surface seat cushion 15 is accommodated in the accommodation concave part 80, the convex part 82a is arranged so that the convex part 82a of the accommodation concave part 80 protrudes toward the sensor 3. The convex part 82a directly applies a pressure to the pressure detection surface 31 of the sensor 3. The area of the sensor 3 is set to be smaller than the area of the first pressing surface 82b and the area of the second pressing surface 15.

The shape of the end having the second pressing surface 15a in the second seating surface seat cushion 15 and the shape of the end forming the installation surface 15b may be set to be substantially the same as the shape of the convex part 82a of the accommodation concave part 80. Being substantially the same means that the case of being identical as well as the case of being recognized as substantially identical even not being identical are included. The same applies to the following. In the state in which the second seating surface seat cushion 15 is accommodated in the accommodation concave part 80, a gap is provided between the outer side surface of the second seating surface seat cushion 15 and the inner side surface of the accommodation concave part 80.

Various dimensions of the accommodation concave part 80 and the second seating surface seat cushion 15 in the state before the accommodation concave part 80 and the second seating surface seat cushion 15 are installed are described with reference to FIG. 4. The width dimension of the opening of the accommodation concave part 80 is defined as c. The width dimension of the convex part 82a and the width dimension of the second seating surface seat cushion 15 are defined as d. In the stacking direction of the first seating surface seat cushion 12 and the second seating surface seat cushion 15, the depth dimension from the counter pressure-receiving surface 12b of the accommodation concave part 80 until the tip end of the convex part 82a are defined as a. In addition, a sum of the thickness dimension of the second seating surface seat cushion 15 and the thickness dimension of the sensor 3 is defined as b.

In the state before the first seating surface seat cushion 12 and the second seating surface seat cushion 15 are installed, it is arranged that a<b. In other words, in the stacking direction of the first seating surface seat cushion 12 and the second seating surface seat cushion 15, the sum b of the thickness dimension of the second seating surface seat cushion 15 and the thickness dimension of the sensor 3 is set to be larger than the depth dimension a from the counter pressure-receiving surface 12b of the accommodation concave part 80 until the tip end of the convex part 82a.

In addition, in the state before the first seating surface seat cushion 12 and the second seating surface seat cushion 15 are installed, it is arranged that c>d. In other words, in the state before the first seating surface seat cushion 12 and the second seating surface seat cushion 15 are installed, the width dimension d of the second seating surface seat cushion 15 is set to be smaller than the width dimension c of the opening of the accommodation concave part 80.

Then, in the state in which the second seating surface seat cushion 15 is accommodated in the accommodation concave part 80 and further installed to the seating surface seat frame 11, various dimensions of the accommodation concave part 80 and the second seating surface seat cushion 15 are described with reference to FIG. 5.

The second seating surface seat cushion 15 is contracted by being sandwiched between the convex part 82a and the seating surface seat frame 11. As a result, the sum of the thickness dimension of the second seating surface seat cushion 15 and the thickness dimension of the sensor 3 is the same as the depth dimension a from the counter pressure-receiving surface 12b of the first seating surface seat cushion 12 until the first pressing surface 82b of the convex part 82a. Accordingly, the pressure detection surface 31 of the sensor 3 is pre-compressed by the first pressing surface 82b of the convex part 82a and the second pressing surface 15a of the second seating surface seat cushion 15. The pre-compression amount at this time is based on the elasticity of the first seating surface seat cushion 12 and the elasticity of the second seating surface seat cushion 15.

Meanwhile, the pre-compression amount with respect to the seating surface seat frame 11 is determined by the self-weight of the first seating surface seat cushion 12. Therefore, the pre-compression amount with respect to the pressure detection surface 31 of the sensor 3 due to the convex part 82 is set to be larger than the pre-compression amount with respect to the seating surface seat frame (equivalent to the periphery of the pressure detection surface 31) due to the first seating surface seat cushion 12. Accordingly, in the state in which the second seating surface seat cushion 15 is accommodated in the accommodation concave part 80 and further installed to the seating surface seat frame 11, the pressure detection surface 31 of the sensor 3 receives a pressure larger than the self-weight of the first seating surface seat cushion 12 from the convex part 82a.

As shown in FIG. 5, in the state in which the second seating surface seat cushion 15 is accommodated in the accommodation concave part 80 and further installed to the seating surface seat frame 11 as well, it is arranged that c>d, and the width dimension d of the second seating surface seat cushion 15 is set to be smaller than the width dimension of the opening of the accommodation concave part 80. That is, a gap is formed between the outer side surface of the second seating surface seat cushion 15 and the inner side surface of the accommodation concave part 80.

1-4. Detailed Configuration of the Sensor-Equipped Seat 1

As the detailed configuration of the sensor-equipped seat 1, the installation state of the sensor 3 and the accommodation concave part 80 is mainly described with reference to FIG. 5. FIG. 5 illustrates a state in which the seated person is not seated at the seat body 2. Thus, in the following, the state in which the seated person is not seated at the seat body 2 is described.

The first seating surface seat cushion 12 is fixed to the seating surface seat frame 11. Accordingly, the periphery of the accommodation concave part 80 in the counter pressure-receiving surface 12b of the first seating surface seat cushion 12 is in contact with the seating surface seat frame 11 in a state of being slightly pre-compressed with respect to the seating surface seat frame 11.

The sensor 3 is disposed between the first pressing surface 82b of the first seating surface seat cushion 12 and the second pressing surface 15a of the second seating surface seat cushion 15. The second seating surface seat cushion 15 is installed to the seating surface seat frame 11.

In addition, the sensor 3 is accommodated in the accommodation concave part 80 of the first seating surface seat cushion 12. The tip end surface of the convex part 82a of the accommodation concave part 80 is in contact with the pressure detection surface 31 of the sensor 3. That is, the pressure detection surface 31 of the sensor 3 receives pressure from the convex part 82a in the first seating surface seat cushion 12. The sensor 3 detects a physical quantity in accordance with the pressure received by the pressure detection surface 31.

In addition, as described above, in the state before the first seating surface seat cushion 12 and the second seating surface seat cushion 15 are installed, the sum b of the thickness dimension of the second seating surface seat cushion 15 and the thickness dimension of the sensor 3 is set to be larger than the depth dimension a from the counter pressure-receiving surface 12b of the accommodation concave part 80 until the tip end part of the convex part 82a. In the state in which the second seating surface seat cushion 15 is accommodated in the accommodation concave part 80 and further installed to the seating surface seat frame 11, the sum of the thickness dimension of the second seating surface seat cushion 15 and the thickness dimension of the sensor 3 is the same as the depth dimension a from the counter pressure-receiving surface 12b of the first seating surface seat cushion until the first pressing surface 82b of the convex part 82a. Therefore, the convex part 82a is pre-compressed with respect to the pressure detection surface 31 of the sensor 3.

In particular, the pre-compression amount with respect to the pressure detection surface 31 of the sensor 3 due to the convex part 82 is set to be sufficiently larger than the pre-compression amount with respect to the seating surface seat frame (equivalent to the periphery of the pressure detection surface 31) due to the first seating surface seat cushion 12. Accordingly, the pressure detection surface 31 of the sensor 3 receives a pressure larger than the self-weight of the first seating surface seat cushion 12.

In the state in which the second seating surface seat cushion 15 is accommodated in the accommodation concave part 80 of the first seating surface seat cushion 12 and no load is applied to the second seating surface seat cushion 15, the second seating surface seat cushion 15 becomes protrusive from the counter pressure-receiving surface 12b of the first seating surface seat cushion 12. By installing the seating surface seat cushion 10 in the state in which the second seating surface seat cushion 15 is protrusive from the first seating surface seat cushion 12 to the installation seating surface 11a of the seating surface seat frame 11, in an unseated state, the counter pressure-receiving surface 12b of the first seating surface seat cushion 12 can be flush with the installation surface 15b facing the installation seating surface 11a among the second seating surface seat cushion 15. Accordingly, since the second seating surface seat cushion 15 can be reliably compressed, the first seating surface seat cushion 12 and the second seating surface seat cushion 15 can be reliably pre-compressed.

1-5. Operation of the Sensor 3

The detection target of the sensor 3 is the seated state of the seated person, such as changes of the seated posture, etc. With the deformation state of the first seating surface seat cushion 12 changing as the seated posture of the seated person changes, the sensor 3 receives the pressure transmitted via the first seating surface seat cushion 12. Specifically, as the seated posture changes, the pressure received by the sensor 3 from the convex part 82a of the first seating surface seat cushion 12 changes. That is, the sensor 3 detects a physical quantity in accordance with the changed pressure, and, based on such physical quantity, detects a change of the seated posture of the seated person.

In addition, other detection targets of the sensor 3 include biological information of the seated person, such as breathing, pulses, heartbeats, etc. Due to breathing, pulses, heartbeats, fine vibrations are generated on the skin surface of the seated person. Due to the fine vibrations, the sensor 3 receives the pressure transmitted via the first seating surface seat cushion 12. Specifically, due to the fine vibrations, the pressure received by the sensor 3 from the convex part 82a of the first seating surface seat cushion 12 changes. That is, the sensor 3 outputs a physical quantity in accordance with the changed pressure, and, based on such physical quantity, detects the biological information of the seated person.

1-6. Effects Due to the Configuration of the Sensor 3

The sensor 3 is disposed between the seating surface seat frame 11 and the counter pressure-receiving surface 12b of the first seating surface seat cushion 12. That is, the sensor 3 is disposed at the seating surface seat frame 11. Accordingly, compared with the case of being disposed in the first seating surface seat cushion 12, the sensor 3 can be positioned stably.

Since the sensor 3 is accommodated in the accommodation concave part 80 provided in the first seating surface seat cushion 12, compared with the case of being installed to the seating surface seat frame 11, the sensor 3 is disposed at a position close to the pressure-receiving surface of the first seating surface seat cushion 12. Thus, the attenuation of the biological signal transmitted from the seated person due to the first seating surface seat cushion 12 is suppressed, so the strength of the biological signal received by the sensor 3 can be increased.

Moreover, since the second seating surface seat cushion 15 is interposed between the sensor 3 and the seating surface seat frame 11, the vibration noise from the vehicle can be attenuated by the second seating surface seat cushion 15.

In addition, since the pre-compression due to the compression reaction force of the first seating surface seat cushion 12 and the second seating surface seat cushion 15 is applied to the sensor 3, when the seated person is seated at the seat body 2, even if the force applied from the seated person to the seating surface seat cushion 10 is small, the force can be transmitted to the sensor 3. As a result, the sensitivity of the sensor 3 can be increased.

1-7. Effects Due to the Flexibility of the Sensor 3

Since the sensor 3 is flexible, when the first seating surface seat cushion 12 is deformed with the seated person being seated at the first seating surface seat cushion 12, the sensor 3 also deforms in accordance with the deformation of the first seating surface seat cushion 12. Accordingly, the noise differing from the pressure from the seated person can be suppressed.

1-8. Effects of the Pre-Compression of the Convex Part 82*a*

The effects due to the sensor 3 in the sensor-equipped seat 1 is described. As described above, in the unseated state in which the seated person is not seated at the seat body 2, in the first seating surface seat cushion 1, the pre-compression amount with respect to the pressure detection surface 31 of the sensor 3 is set to be larger than the pre-compression amount with respect to the periphery (e.g., the seating surface seat frame 11) of the pressure detection surface 31.

Accordingly, in the unseated state, a stress larger than that in other portions has been generated at the convex part 82*a* in the first seating surface seat cushion 12. The convex part 82*a* is pre-compressed in the normal direction of the pressure detection surface 31 of the sensor 3. Accordingly, in the first seating surface seat cushion 12, a largest stress is generated at the convex part 82*a*, and a stress larger than that of other portions is generated within the range from the convex part 82*a* until the pressure-receiving surface 12*a* of the first seating surface seat cushion 12. Therefore, in the unseated state, the sensor 3 has received pressure from the convex part 82*a*.

Then, the case where the seated person is seated at the seat body 2 is considered. With the seated person being seated at the seat body 2, a force is applied from the buttocks of the seated person to the first seating surface seat cushion 12. Thus, the first seating surface seat cushion 12 deforms in accordance with the buttocks and the body weight of the seated person. In addition, compared with the unseated state, the magnitude of the stress generated in the first seating surface seat cushion 12 is larger in the seated state. However, even in the seated state, in the first seating surface seat cushion 12, the largest stress is generated at the convex part 82*a*, and a stress larger than that in other portions is generated within the range from the convex part 82*a* until the pressure-receiving surface 12*a* of the first seating surface seat cushion 12.

Here, one of the detection targets of the sensor 3 is the seated state of the seated person, such as the change of the seated posture. In addition, other detection targets of the sensor 3 include biological information of the seated person, such as breathing, pulses, heartbeats, etc.

In addition, with the pressure detection surface 31 of the sensor 3 receiving pressure from the convex part 82*a* of the first seating surface seat cushion 12, the sensor 3 detects the seated state of the seated person or the biological information of the seated person. However, the first seating surface seat cushion 12 absorbs the force applied from the seated person. Therefore, even if a force is applied to the pressure-receiving surface 12*a* of the first seating surface seat cushion 12 due to changes of the seated state of the seated person or vibrations generated by a living body, if the first seating surface seat cushion 12 absorbs all of the force, the sensor 3 is unable to detect the seated state or the biological information of the seated person.

Nevertheless, as described above, the pre-compression applied by the first seating surface seat cushion 12 is applied to the pressure detection surface 31 of the sensor 3 in the unseated state. However, in the unseated state, the first seating surface seat cushion 12 also applies pre-compression to the periphery (seating surface seat frame 11) of the pressure detection surface 31 of the sensor 3. In addition, in the first seating surface seat cushion 12 and in the unseated state, the pre-compression amount with respect to the pressure detection surface 31 of the sensor 3 is set to be larger than the pre-compression amount with respect to the periphery of the pressure detection surface 31.

In this way, by setting the pre-compression amount with respect to the pressure detection surface 31 of the sensor 3 to be larger than the periphery, when the seated person is seated at the sheet body 2, even if the force applied to the first seating surface seat cushion 12 from the seated person is very small, such force is still transmitted to the pressure detection surface 31 of the sensor 3. Accordingly, the pressure detection surface 31 of the sensor 3 can detect fine pressure changes applied to the first seating surface seat cushion 12.

That is, even if the seated state of the seated person merely changes slightly, the pressure detection surface 31 of the sensor 3 can detect a fine pressure change that is transmitted together with the change. Accordingly, the seated state of the seated person can be detected at high precision. In addition, the magnitudes of the force applied from the seated person to the first seating surface seat cushion 12 due to vibrations caused by a living body such as breathing, pulses, and heartbeats are small. In such case as well, the pressure detection surface 31 of the sensor 3 can detect fine pressure changes transmitted together with the vibrations generated by the living body. Accordingly, the biological information of the seated person can be detected at high precision.

In particular, as described above, in the unseated state, in the first seating surface seat cushion 12, the largest stress is generated at the convex part 82*a*, and a stress larger than that in other portions is generated within the range from the convex part 82*a* to the pressure-receiving surface 12*a* of the first seating surface seat cushion 12. Therefore, compared with other regions, the region where a stress is generated in the unseated state has a higher power transmission sensitivity.

Accordingly, even if the force applied to the pressure-receiving surface 12a of the first seating surface seat cushion 12 is small, the small force is transmitted, with high sensitivity, through the range from the pressure-receiving surface 12a of the first seating surface seat cushion 12 to the pressure detection surface 31 of the sensor 3 via the convex part 82a. As a result, the seated state or the biological information of the seated person can be detected at high precision.

In addition, regarding the first seating surface seat cushion 12 having the pressure-receiving surface 12a where the seated person is seated, an elastic modulus taking into consideration the sitting comfort of the seated person may be set. Meanwhile, in the case where the pre-compression amount applied to the sensor 3 is considered, it is not limited that the elastic modulus of the first seating surface seat cushion 12 taking into consideration the sitting comfort is optimal. In such case, by making the elastic modulus of the second seating surface seat cushion 15 and the elastic modulus of the first seating surface seat cushion 12 different from each other, the pre-compression amount applied to the sensor 3 can be properly adjusted. Accordingly, the sensitivity of the sensor 3 can be increased.

The first cushion includes the recessed groove 82c formed at the bottom part 82 of the accommodation concave part 80, formed along the edge of the convex part 82a, and separating the outer side surface of the convex part 82a and the inner side surface of the accommodation concave part 80.

Since the outer side surface of the convex part 82a and the inner side surface of the accommodation concave part 80 are separated by the recessed groove 82c, when the force applied to the pressure-receiving surface 12a of the first cushion from the seated person is transmitted to the sensor 3 from the convex part 82a, the generation of the friction force due to the sliding contact between the outer side surface of the convex part 82a and the inner side surface of the accommodation concave part 80 can be suppressed. Accordingly, since the attenuation of the force applied from the seated person to the pressure-receiving surface 12a of the first seating surface seat cushion 12 due to friction is suppressed, the sensitivity of the sensor 3 can be increased.

In addition, with the first seating surface seat cushion 12 being covered by the seating surface skin member 13, the first seating surface seat cushion 12 is prevented from deforming to expand outward. Accordingly, the decrease in the pre-compression amount due to the pre-compressed first seating surface seat cushion 12 expanding outward is suppressed. As a result, compared with the case where the first seating surface seat cushion 12 is not covered by the seating surface skin member 13, the decrease in the sensitivity of the sensor 3 is suppressed.

Embodiment 2

The sensor-equipped seat 1 of the embodiment is described with reference to FIGS. 6 and 7. The embodiment differs from Embodiment 1 in the point that a first seating surface seat cushion 112 of the sensor-equipped seat 1 of the embodiment does not have the convex part 82a. The bottom surface of an accommodation concave part 180 is arranged as a first pressing part 182b pressing the sensor 3. It is noted that, unless otherwise specified, among the reference numerals used in Embodiment 2 and subsequent embodiments, the same reference numerals as those used in the previously described embodiments represent the same components as those in the previously described embodiments.

Figure 6:
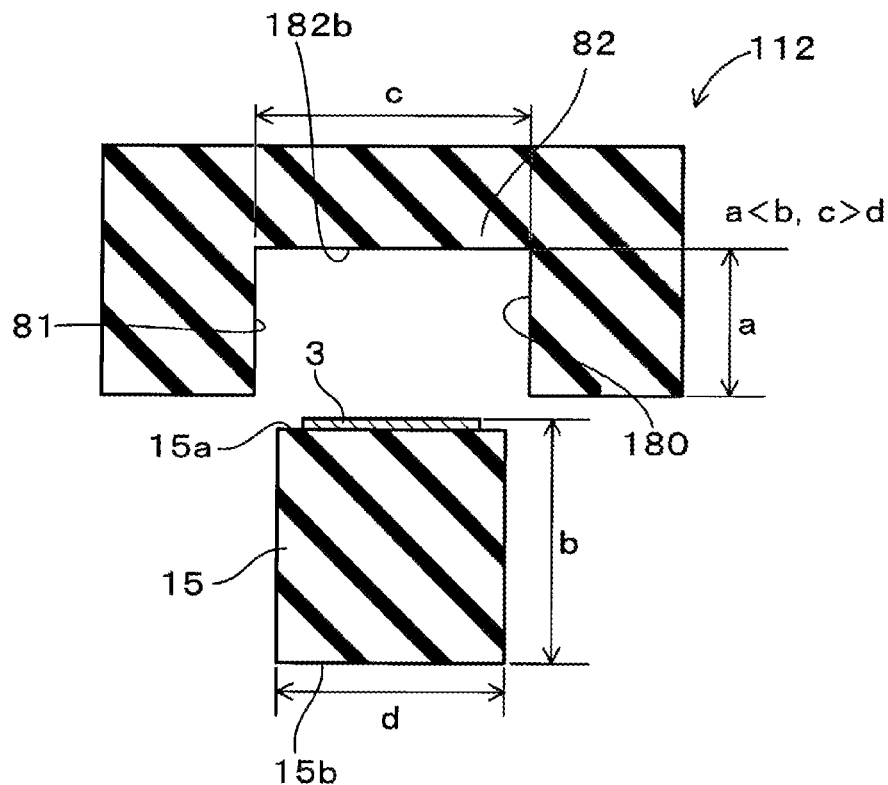
FIG. 6 is a partial cross-sectional view illustrating a state before a first seating surface seat cushion and a second seating surface seat cushion are installed in a sensor-equipped seat of Embodiment 2.
Figure 7:
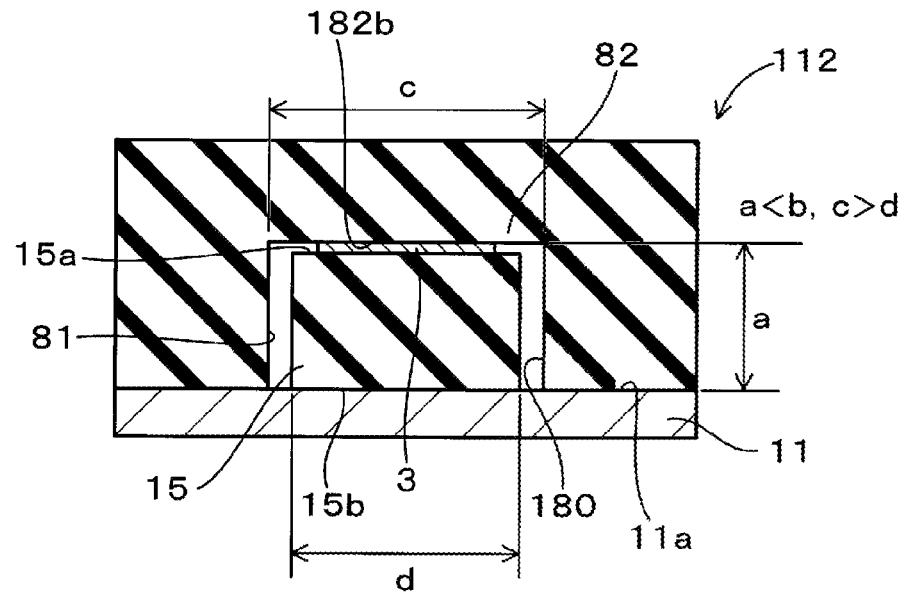
FIG. 7 is a partial cross-sectional view illustrating a state in which the first seating surface seat cushion and the second seating surface seat cushion of Embodiment 2 are installed and further installed to a seating surface seat frame.

As shown in FIG. 6, in the stacking direction of the first seating surface seat cushion 112 and the second seating surface seat cushion 15, a depth dimension from the counter pressure-receiving surface 12b of the accommodation concave part 180 until the first pressing surface 182b is defined as a. In addition, a sum of the thickness dimension of the second seating surface seat cushion 15 and the thickness dimension of the sensor 3 is defined as b.

In the embodiment, in the state before the first seating surface seat cushion 112 and the second seating surface seat cushion 15 are installed, it is arranged that a<b. In other words, in the stacking direction of the first seating surface seat cushion 112 and the second seating surface seat cushion 15, the sum b of the thickness dimension of the second seating surface seat cushion 15 and the thickness dimension of the sensor 3 is set to be larger than the depth dimension a from the counter pressure-receiving surface 12b of the accommodation concave part 180 until the first pressing surface 182b.

Then, in the state in which the second seating surface seat cushion 15 is accommodated in the accommodation concave part 180 and further installed to the seating surface seat frame 11, various dimensions of the accommodation concave part 180 and the second seating surface seat cushion 15 are described with reference to FIG. 7.

In the state in which the second seating surface seat cushion 15 is accommodated in the accommodation concave part 180 and further installed to the seating surface seat frame 11, the counter pressure-receiving surface 12b of the first seating surface seat cushion 112, the installation surface 15b of the second seating surface seat cushion 15, and the installation surface 11a of the seating surface seat frame 11 are flush. Accordingly, the second seating surface seat cushion 15 is formed to be able to apply pre-compression with respect to the sensor 3.

Embodiment 3

Next, the sensor-equipped seat 1 of Embodiment 3 is described with reference to FIGS. 8 and 9. The embodiment differs from Embodiment 2 in the point that the sensor-equipped seat 1 of the embodiment includes an elastic layer 90 that is elastically deformable between the first seating surface seat cushion 112 and the sensor 3.

The elastic layer 90 is stacked on a pressure detection surface 42 of the sensor 3. The elastic layer 90 is formed by an elastically deformable resin or elastomer, etc., and an arbitrary material can be selected. The elastic modulus of the elastic layer 90 may be the same as or different from the elastic modulus of the first seating surface seat cushion 112. In addition, the elastic modulus of the elastic layer 90 may be the same as or different from the elastic modulus of the second seating surface seat cushion 15. As the resin forming the elastic layer 90, examples may include polyolefin-based resins and polyamide-based resins. As the elastomer, examples may include urethane-based elastomers, acrylic-based elastomers, ester-based elastomers, polyamide-based elastomers, olefin-based elastomers, and styrene-based elastomers.

Figure 8:
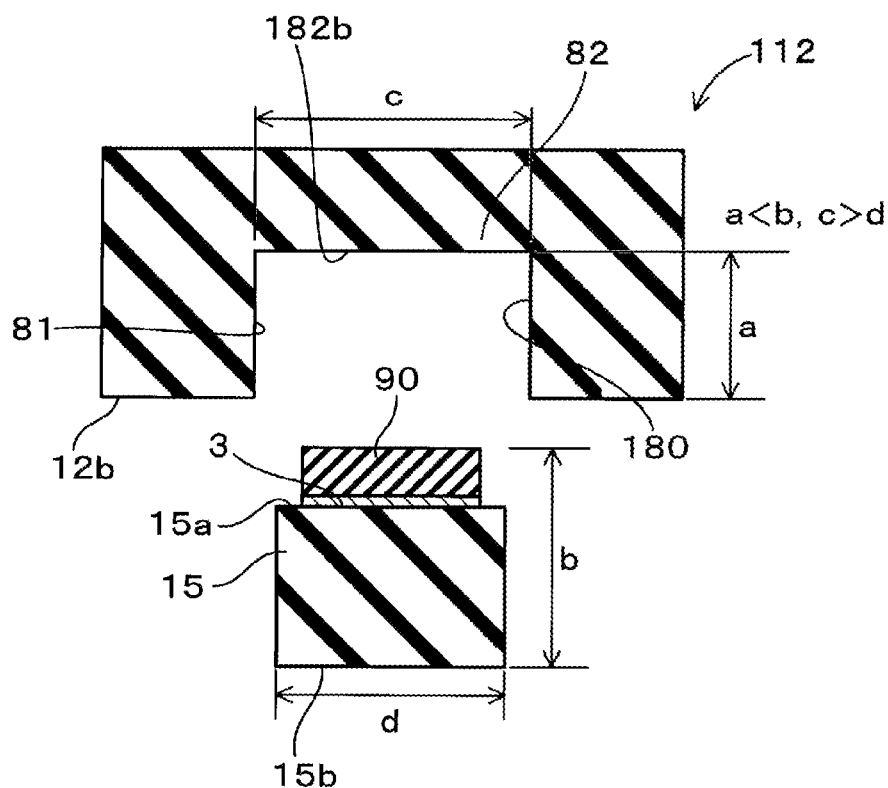
FIG. 8 is a partial cross-sectional view illustrating a state before a first seating surface seat cushion and a second seating surface seat cushion are installed in a sensor-equipped seat of Embodiment 3.
Figure 9:
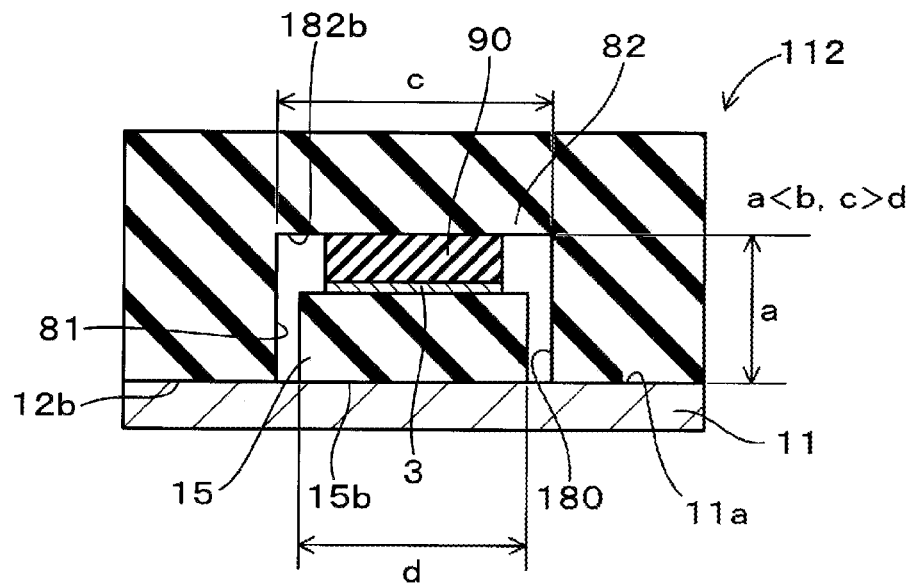
FIG. 9 is a partial cross-sectional view illustrating a state in which the first seating surface seat cushion and the second seating surface seat cushion of Embodiment 3 are installed and further installed to a seating surface seat frame.

As shown in FIG. 8, in the stacking direction of the first seating surface seat cushion 112 and the second seating surface seat cushion 15, a depth dimension from the counter pressure-receiving surface 12b of the accommodation concave part 180 until the first pressing surface 182b is defined as a. In addition, a sum of the thickness dimension of the second seating surface seat cushion 15, the thickness dimension of the sensor 3, and the thickness of the elastic layer 90 is defined as b.

In the embodiment, in the state before the first seating surface seat cushion 12 and the second seating surface seat cushion 15 are installed, it is arranged that a<b. In other words, in the stacking direction of the first seating surface seat cushion 112 and the second seating surface seat cushion 15, the sum b of the thickness dimension of the second seating surface seat cushion 15, the thickness dimension of the sensor 3, and the thickness dimension of the elastic layer 90 is set to be larger than the depth dimension a from the counter pressure-receiving surface 12b of the accommodation concave part 180 until the first pressing surface 182b.

Then, in the state in which the second seating surface seat cushion 15 is accommodated in the accommodation concave part 180 and further installed to the seating surface seat frame 11, various dimensions of the accommodation concave part 180 and the second seating surface seat cushion 15 are described with reference to FIG. 9.

In the state in which the second seating surface seat cushion 15 is accommodated in the accommodation concave part 180 and further installed to the seating surface seat frame 11, the counter pressure-receiving surface 12b of the first seating surface seat cushion 112, the installation surface 15b of the second seating surface seat cushion 15, and the installation surface 11a of the seating surface seat frame 11 are flush. Accordingly, the second seating surface seat cushion 15 is formed to be able to apply pre-compression with respect to the sensor 3.

Since the elastic layer 90 is provided between the first seating surface seat cushion 112 and the sensor 3, by changing the material forming the elastic layer 90, the elastic modulus of the elastic layer 90, the thickness dimension of the elastic layer 90, etc., the amount of pre-compression applied to the sensor 3 from the first seating surface seat cushion 112 can be adjusted. Accordingly, the sensitivity of the sensor 3 can be adjusted.

In addition, in the embodiment, the area of the elastic layer 90 is equal to or less than the area of the pressure detection surface 31 of the sensor 3. Accordingly, in the state in which the second seating surface seat cushion 15 is accommodated in the accommodation concave part 180 and further installed to the seating surface seat frame 11, the pre-compression amount with respect to the pressure detection surface 31 is set to be larger than the pre-compression amount with respect to the seating surface seat frame 11 (periphery of the pressure detection surface). Accordingly, even if the force applied to the first seating surface seat cushion 112 from the seated person when the seated person is seated at the seat 1 is small, the small force can be transmitted, with high sensitivity, through the range from the pressure-receiving surface 12a of the first seating surface seat cushion 112 to the pressure detection surface 31 of the sensor 3 via the elastic layer 90. As a result, the seated state or the biological information of the seated person can be detected at high precision.

Embodiment 4

Next, the sensor-equipped seat 1 of Embodiment 4 is described with reference to FIGS. 10 and 11. The embodiment differs from Embodiment 2 in the point that the sensor-equipped seat 1 of the embodiment includes an elastic layer 90 that is elastically deformable between the sensor 3 and the second seating surface seat cushion 15.

The elastic layer 90 is stacked on the second pressing surface 15a of the second seating surface seat cushion 15. The elastic layer 90 of the embodiment is the same as Embodiment 3. Therefore, repeated description is omitted.

Figure 10:
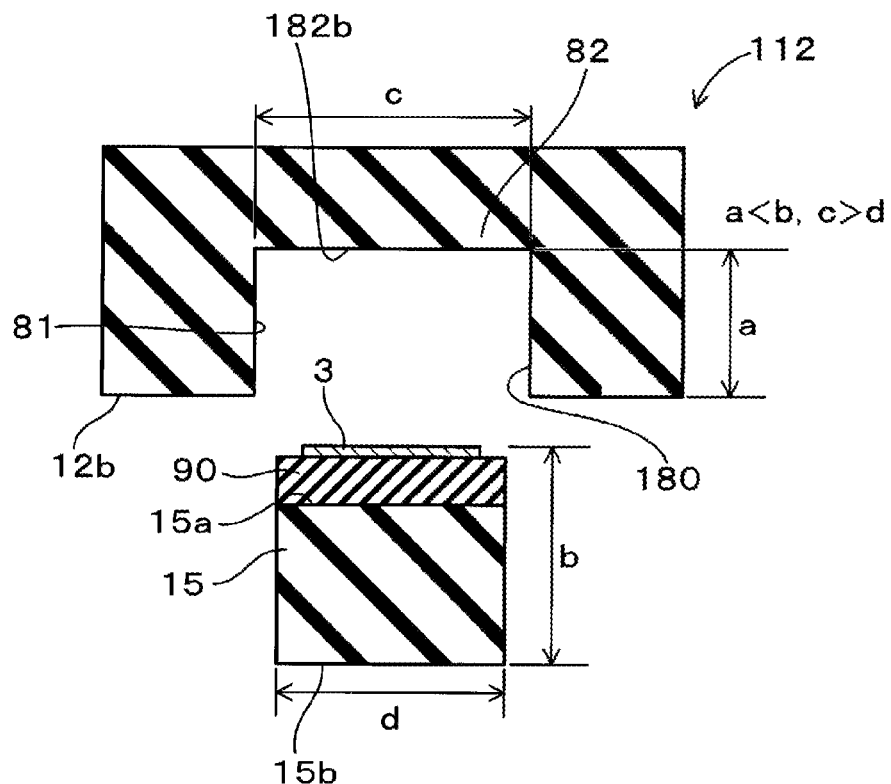
FIG. 10 is a partial cross-sectional view illustrating a state before a first seating surface seat cushion and a second seating surface seat cushion are installed in a sensor-equipped seat of Embodiment 4.
Figure 11:
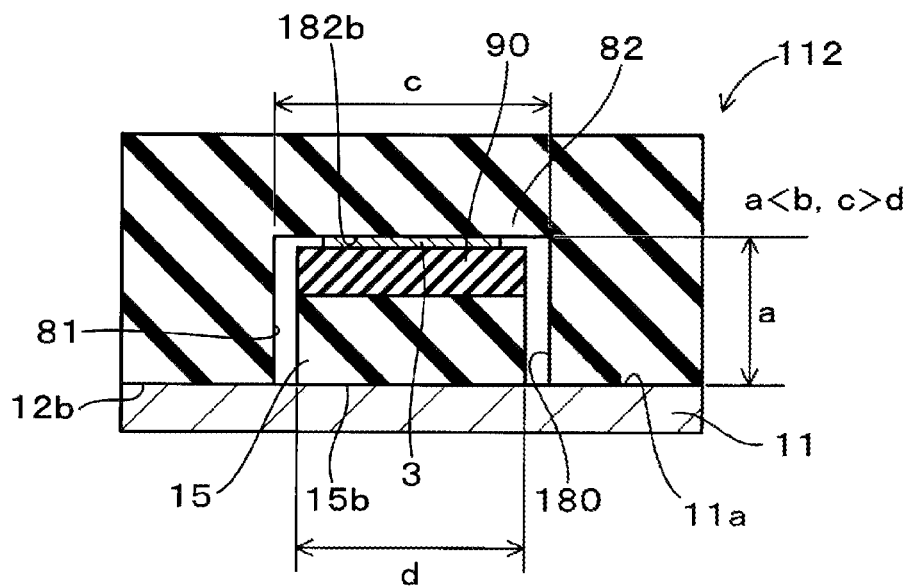
FIG. 11 is a partial cross-sectional view illustrating a state in which the first seating surface seat cushion and the second seating surface seat cushion of Embodiment 4 are installed and further installed to a seating surface seat frame.

As shown in FIG. 10, in the stacking direction of the first seating surface seat cushion 112 and the second seating surface seat cushion 15, a depth dimension from the counter pressure-receiving surface 12b of the accommodation concave part 180 until the first pressing surface 182b is defined as a. In addition, a sum of the thickness dimension of the second seating surface seat cushion 15, the thickness dimension of the elastic layer 90, and the thickness of the sensor 3 is defined as b.

In the embodiment, in the state before the first seating surface seat cushion 112 and the second seating surface seat cushion 15 are installed, it is arranged that a<b. In other words, in the stacking direction of the first seating surface seat cushion 112 and the second seating surface seat cushion 15, the sum b of the thickness dimension of the second seating surface seat cushion 15, the thickness dimension of the elastic layer 90, and the thickness dimension of the sensor 3 is set to be larger than the depth dimension a from the counter pressure-receiving surface 12b of the accommodation concave part 180 until the first pressing surface 182b.

Then, in the state in which the second seating surface seat cushion 15 is accommodated in the accommodation concave part 180 and further installed to the seating surface seat frame 11, various dimensions of the accommodation concave part 180 and the second seating surface seat cushion 15 are described with reference to FIG. 11.

In the state in which the second seating surface seat cushion 15 is accommodated in the accommodation concave part 180 and further installed to the seating surface seat frame 11, the counter pressure-receiving surface 12b of the first seating surface seat cushion 112, the installation surface 15b of the second seating surface seat cushion 15, and the installation surface 11a of the seating surface seat frame 11 are flush. Accordingly, the second seating surface seat cushion 15 is formed to be able to apply pre-compression with respect to the sensor 3.

Since the elastic layer 90 is provided between the second seating surface seat cushion 15 and the sensor 3, by changing the material forming the elastic layer 90, the elastic modulus of the elastic layer 90, the thickness dimension of the elastic layer 90, etc., the amount of the pre-compression applied to the sensor 3 from the second seating surface seat cushion 15 can be adjusted. Accordingly, the sensitivity of the sensor 3 can be adjusted.

However, it may also be configured that an elastic layer is arranged between the first seating surface seat cushion 112 and the sensor 3, and the elastic layer 90 is further arranged between the second seating surface seat cushion 15 and the sensor 3.

Embodiment 5

Next, the sensor-equipped seat 1 of Embodiment 5 is described with reference to FIG. 12. The embodiment differs from Embodiment 1 in the point that a sensor 103 of the sensor-equipped seat 1 of the embodiment includes a sensor elastic layer 91 between the first film sheet 30 and the first electrode sheet 32.

Figure 12:
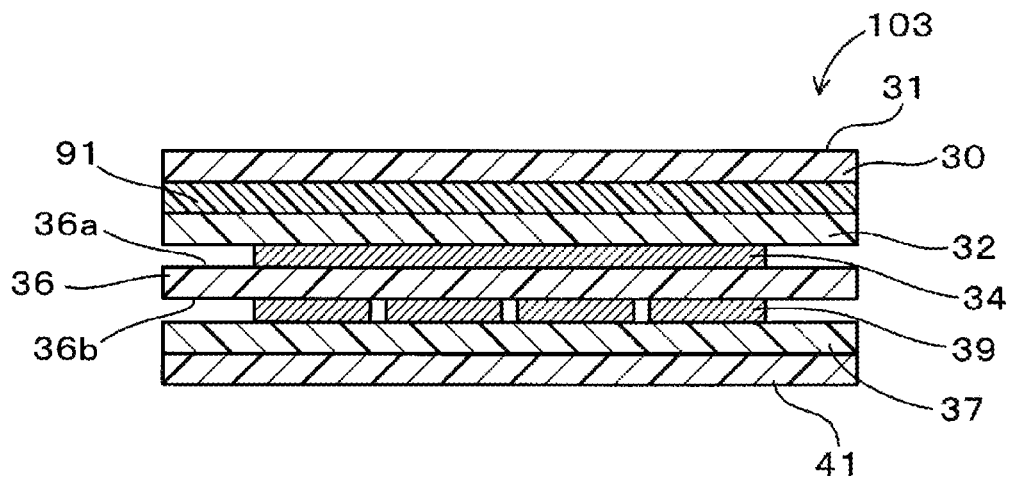
FIG. 12 is a cross-sectional view illustrating a sensor forming a sensor-equipped seat according to Embodiment 5.

As shown in FIG. 12, the sensor 103 of the embodiment has the elastically deformable sensor elastic layer 91 between the first film sheet 30 and the first electrode sheet 32. The sensor elastic layer 91 is formed in a rectangular shape, and is set to have an area substantially the same as the areas of the first film sheet 30 and the first electrode sheet 32. Since the material forming the sensor elastic layer 91 of the embodiment is the same as the elastic layer 90 of Embodiment 3, repeated description is omitted.

With the sensor 103 being provided with the sensor elastic layer 91, the amount of the pre-compression applied from the first seating surface seat cushion 12 and the second seating surface seat cushion 15 can be finely adjusted in the sensor 103. Accordingly, the sensitivity of the sensor 103 can be finely adjusted.

In addition, with the sensor elastic layer 91 being arranged between the first film sheet 30 and the first electrode sheet 32, the amount of the pre-compression applied from the first seating surface seat cushion 12 can be adjusted.

Embodiment 6

Next, the sensor-equipped seat 1 of Embodiment 6 is described with reference to FIG. 13. The embodiment differs from Embodiment 1 in the point that a sensor 203 of the sensor-equipped seat 1 of the embodiment includes the sensor elastic layer 91 between the second film sheet 41 and the second electrode sheet 37.

Figure 13:
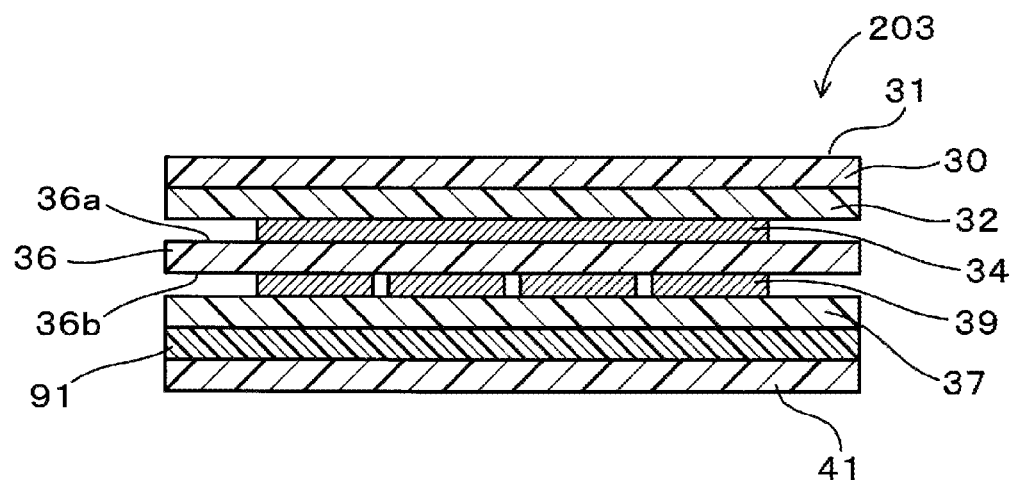
FIG. 13 is a cross-sectional view illustrating a sensor forming a sensor-equipped seat according to Embodiment 6.

As shown in FIG. 13, the sensor 203 of the embodiment has the elastically deformable sensor elastic layer 91 between the second film sheet 41 and the second electrode sheet 37. The sensor elastic layer 91 is formed in a rectangular shape, and is set to have an area substantially the same as the areas of the second film sheet 41 and the second electrode sheet 37. Since the material forming the sensor elastic layer 91 of the embodiment is the same as the elastic layer 90 of Embodiment 3, repeated description is omitted.

In addition, by arranging the sensor elastic layer 91 between the second film sheet 41 and the second electrode sheet 37, the vibration noise from the vehicle can be reduced.

By forming the insulator sheet 36 by using an elastically deformable material, the insulator sheet 36 may also serve as a sensor elastic layer. In such case, the sensitivity of the sensor 3 can be finely adjusted by increasing the number of parts.

Embodiment 7

Next, the sensor-equipped seat 1 of Embodiment 7 is described with reference to FIG. 14. The embodiment differs from Embodiment 2 in the point that, in the sensor-equipped sheet 1 of the embodiment, the seating surface seat frame 111 includes a pressing convex part 111b.

Figure 14:
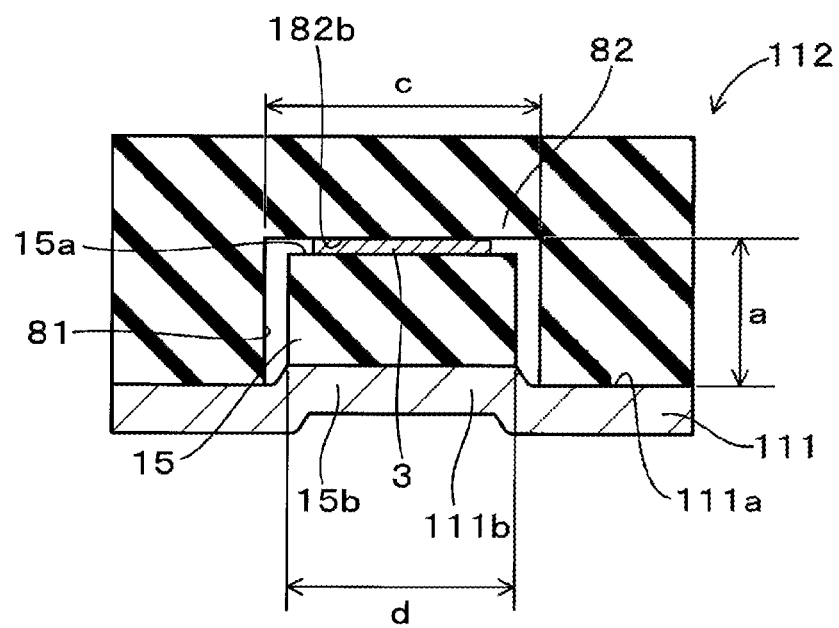
FIG. 14 is a partial cross-sectional view illustrating a state in which a first seating surface seat cushion and a second seating surface seat cushion are installed and further installed to a seating surface seat frame in a sensor-equipped seat of Embodiment 7.

As shown in FIG. 14, the pressing convex part 111b is formed on an installation seating surface 111a of the seating surface seat frame 111. The pressing convex part 111b protrudes toward the second seating surface seat cushion 15.

When the first seating surface seat cushion 112 and the second seating surface seat cushion 15 are installed to the installation seating surface 111a of the seating surface seat frame 111, the pressing convex part 112b provided on the installation seating surface 111a presses the second seating surface seat cushion 15. Accordingly, the second seating surface seat cushion 15 can be pre-compressed reliably. As a result, the sensitivity of the sensor 3 can be increased.

Embodiment 8

Figure 15:
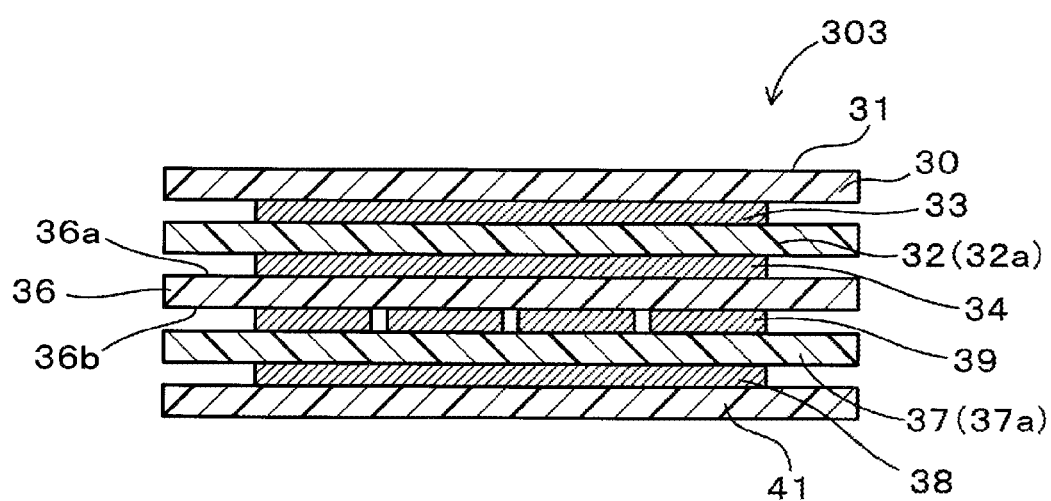
FIG. 15 is a cross-sectional view illustrating a sensor forming a sensor-equipped seat according to Embodiment 8.

Next, a sensor 303 of Embodiment 8 is described with reference to FIG. 15. The sensor 303 of the embodiment includes a first shield layer 33 and a second shield layer 38.

The first electrode sheet 32 of the embodiment includes the first electrode layer 34 disposed on a surface (the lower surface of FIG. 15) facing the first surface 36a of the insulator sheet 36 among the first body part 32a formed by an insulation sheet. In addition, the first shield layer 33 is stacked on a surface on the side opposite to the surface where the first electrode layer 34 is formed in the first electrode sheet 32. The first shield layer 33 is formed by a metal coil, a conductive cloth, a conductive film, etc., having a conductive property. While not shown in detail, the first shield layer 33 is grounded.

The second electrode sheet 37 of the embodiment includes the second electrode layer 39 disposed on a surface (the lower surface of FIG. 15) facing the second surface 36b of the insulator sheet 36 among the second body part 37a formed by an insulation sheet. In addition, the second shield layer 38 is formed on a surface on the side opposite to the surface where the second electrode layer 39 is formed in the second electrode seat 37. The second shield layer 38 is formed by a metal coil, a conductive cloth, a conductive film, etc., having a conductive property. While not shown in detail, the second shield layer 38 is grounded.

The sensor 303 of the embodiment is protected from electromagnetic noises from the top and the bottom of the sensor 303 by using the first shield layer 33 and the second shield layer 38.

Embodiment 9

9-1. Ventilation Configuration of the Sensor-Equipped Seat

Figure 16:
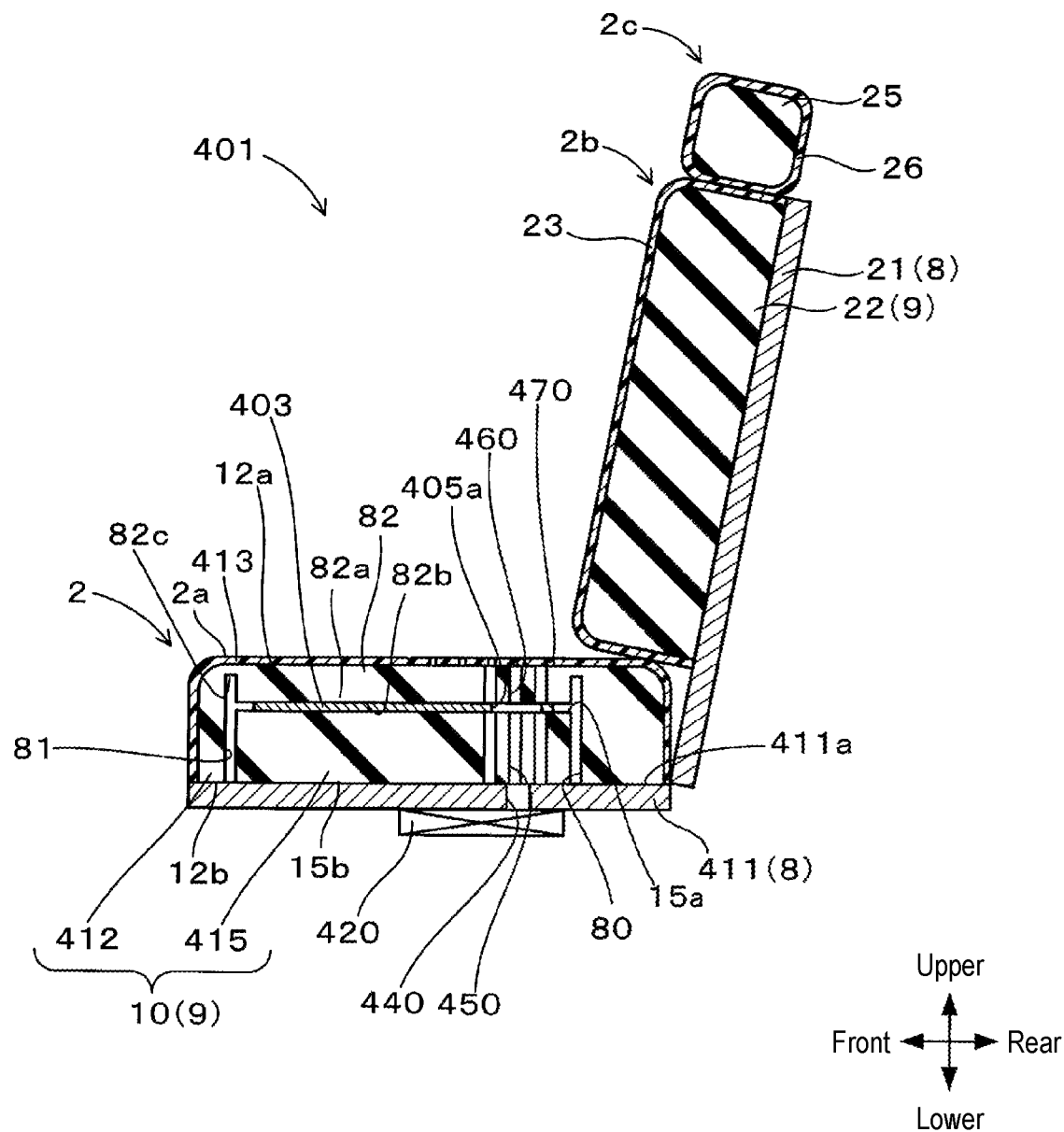
FIG. 16 is a cross-sectional view of a sensor-equipped seat of Embodiment 9, and is a cross-sectional view taken along a line XVI-XVI of FIG. 19.

Next, a sensor-equipped seat 401 of Embodiment 9 is described with reference to FIGS. 16 to 19. FIG. 16 illustrates the sensor-equipped seat 401 of the embodiment. In the following description, upper-lower, front-rear, and left-right directions refer to the upper-lower, front-rear, and left-right directions viewed from the seated person in the state in which the seated person is seated at the seat 401.

As shown in FIG. 16, a seating surface seat frame 411 includes a ventilation device 420. In the embodiment, although the ventilation device 420 is installed to a surface on a side opposite to an installation surface 411a in the seating surface seat frame 411, the installation position of the ventilation device 420 is not particularly limited, and the ventilation device 420 may also be installed to the installation seating surface 411a.

The ventilation device 420 is configured to blow wind upward or downward in FIG. 16. Accordingly, the ventilation device 420 circulates air from the seating surface seat frame 411 to a second seating surface seat cushion 415, a first seating surface seat cushion 412, and a seating surface skin member 413. As the ventilation device 420, for example, a conventional configuration having a motor and a fan can be adopted.

The seating surface seat frame 411 has a frame through hole 440 penetrating in the thickness direction (the upper-lower direction of FIG. 16) of the seating surface seat frame 411. By using the ventilation device 420, the air is configured to be able to circulate in the frame through hole 440.

Figure 17:
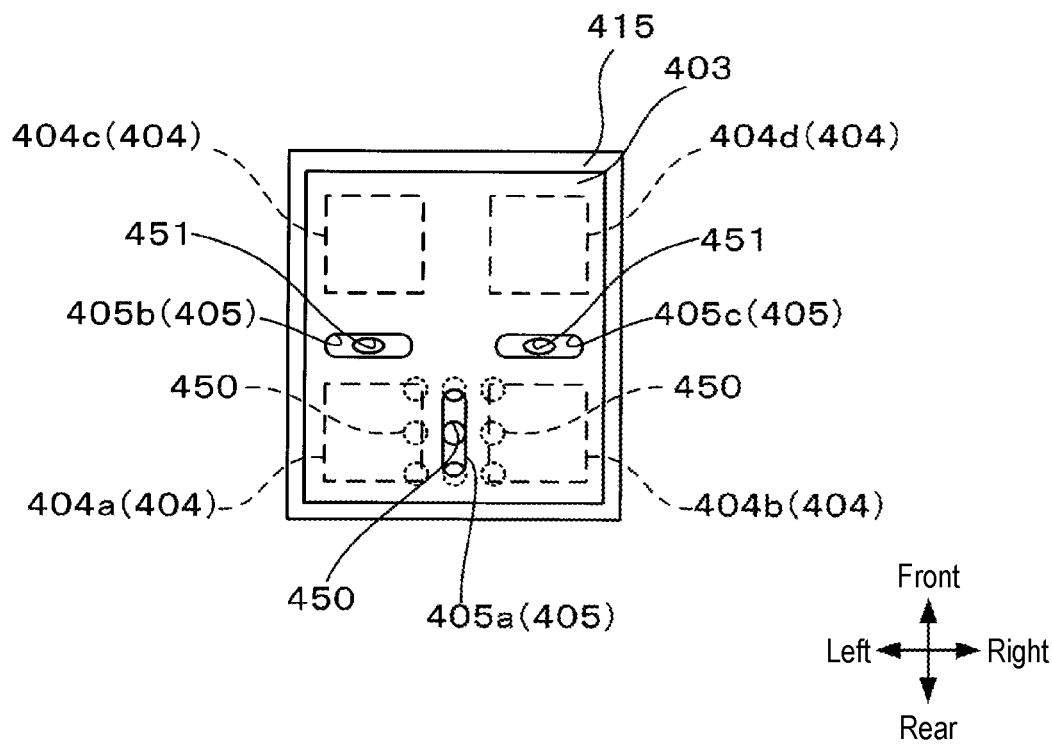
FIG. 17 is a plan view illustrating a sensor and a second seating surface seat cushion forming the sensor-equipped seat of Embodiment 9.

As shown in FIG. 16, in the direction in which the first seating surface seat cushion 412 and the second seating surface seat cushion 415 are stacked (the upper-lower direction of FIG. 16, which is referred to as "stacking direction" in the following), the second seating surface seat cushion 415 is provided with a second ventilation passage 450 penetrating through the second seating surface seat cushion 415 at a position overlapped with the frame through hole 440. The second seating surface seat cushion 415 may include one second ventilation passage 450, and may also include two or more second ventilation passages 450. As shown in FIG. 17, in the embodiment, nine second ventilation passages 450 are formed at the second seating surface seat cushion 415. The second ventilation passage 450 penetrates through the second seating surface seat cushion 415 in the stacking direction (see FIG. 16).

As shown in FIG. 17, the sensor 403 has a ventilation through hole 405 penetrating through the sensor 403 in the stacking direction at a position overlapped with the second ventilation passage 450 when projected in the stacking direction. The inner shape of the ventilation through hole 405 may be the same as or different from the inner shape of the second ventilation passage 450. The ventilation through hole 405 of the embodiment is formed in a shape of an elongated hole. However, the shape of the ventilation through hole 405 is not particularly limited, and an arbitrary shape, such as a circular shape, an elongated rectangular shape can be selected.

As shown in FIG. 16, a first ventilation passage 460 penetrating through the first seating surface seat cushion 412 in the stacking direction is provided at a position overlapped with the second ventilation passage 450 in the stacking direction in the first seating surface seat cushion 412. The first ventilation passage 460 penetrates through the first seating surface seat cushion 415 in the stacking direction. The ventilation through hole 405 is formed at a position overlapped with the first ventilation passage 460 and the second ventilation passage 450 when projected in the stacking direction.

Figure 18:
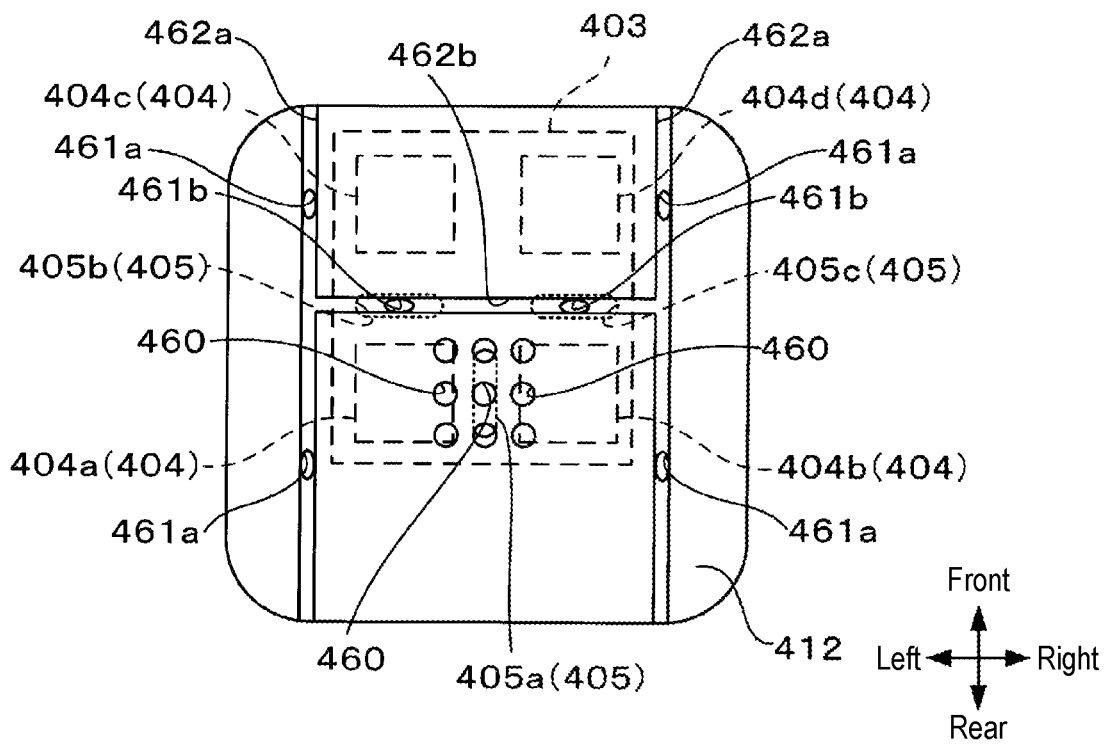
FIG. 18 is a plan view illustrating a first seating surface seat cushion forming the sensor-equipped seat of Embodiment 9.

As shown in FIG. 18, in the embodiment, nine first ventilation passages 460 are formed at the first seating surface seat cushion 412. The first ventilation passage 460 penetrates through the first seating surface seat cushion 415 in the stacking direction. As shown in FIGS. 17 and 18, the first ventilation passage 460 and the second ventilation passage 450 are formed at an integrated position in the stacking direction. However, it may also be that the first ventilation passage 460 and the second ventilation passage 450 are formed at substantially overlapped positions, instead of being formed at the integrated position in the stacking direction. The first seating surface seat cushion 412 is formed by a foam material and thus has multiple pores. Since it is possible for the air to flow through the pores, it may also be configured that air is able to flow between the first ventilation passage 460 and the second ventilation passage 450 even if the air first ventilation passage 460 and the second ventilation passage 450 are not integrated in the stacking direction.

Figure 19:
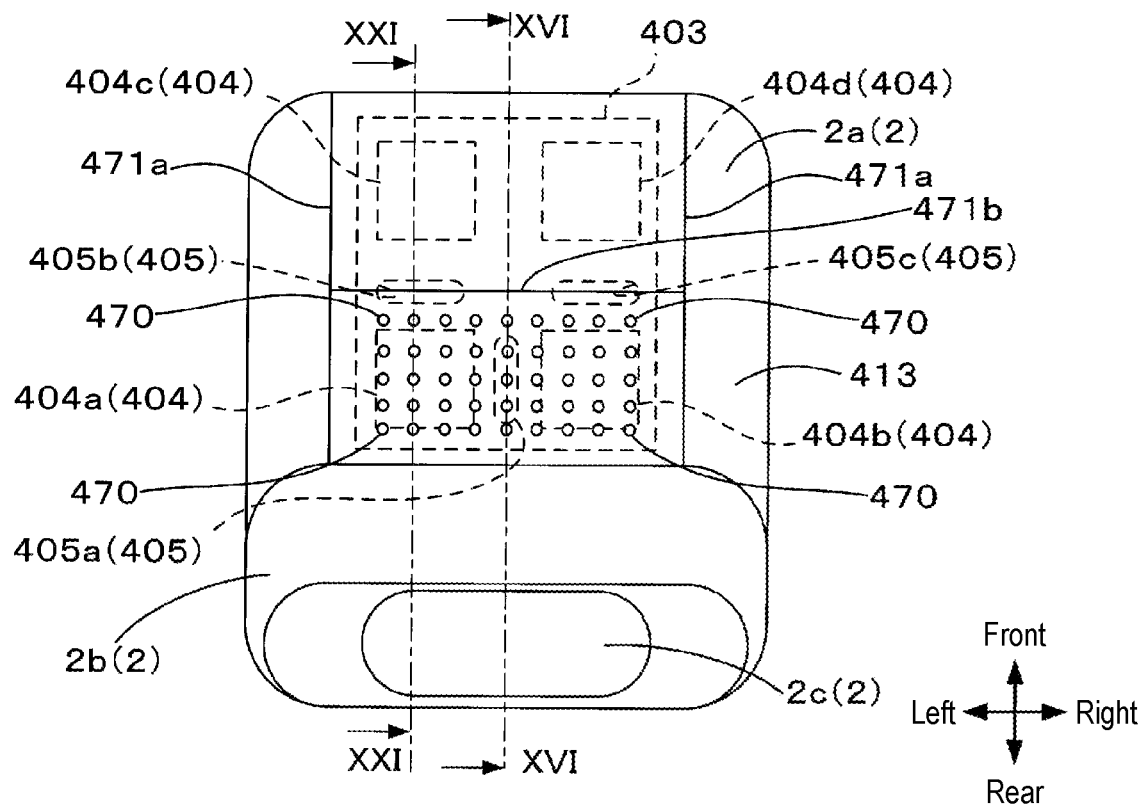
FIG. 19 is a plan view illustrating the sensor-equipped seat according to Embodiment 9.

As shown in FIG. 19, a seating surface skin member 413 includes a skin through hole 470 penetrating through the seating surface skin member 413 in the stacking direction. In the embodiment, it may also be configured that multiple skin through holes 470 are formed at intervals. The inner diameter dimension of the skin through hole 470 is set to be smaller than the inner diameter dimension of the first ventilation passage 460.

The skin through hole 470 may also be formed at a position overlapped with the first ventilation passage 460 of the first seating surface seat cushion 412 in the stacking direction. Accordingly, air can pass through the skin through hole 470 and arrive at the top of the seating surface skin member 413.

In addition, in the case where the skin through hole 470 is formed in the vicinity of the first ventilation passage 460 of the first seating surface seat cushion 412 in the stacking direction, the skin through hole 470 may also be formed at a position not overlapped with the first ventilation passage 460. As described above, the first seating surface seat cushion 412 is formed by foam resin, etc. Thus, multiple pores are provided in the first seating surface seat cushion 412. Accordingly, when air flows until the first ventilation passage 460, the air can arrive at the seating surface skin member 413 through the pores. As a result, in the case where the skin through hole 470 is formed in the vicinity of the first ventilation passage 460 of the first seating surface seat cushion 412, the air arrives at the skin through hole 470 by flowing in the pores, and can arrive over the seating surface skin member 413.

As shown in FIG. 19, multiple skin through holes 470 are formed in a region between two side suspension grooves 471a and rearward of a central suspension groove 471 to be described afterwards, in the seating surface skin member 413. In other words, the skin through holes 470 are located at positions near the back surface seat cushion 22, and are formed in regions corresponding to the buttocks of the seated person. However, the skin through holes 470 may also be formed at positions different from the positions corresponding to the buttocks of the seated person. The inner shape of the skin through hole 470 may be circular, polygonal (such as being rectangular), etc., and an arbitrary shape can be selected as appropriate.

9-2. Structure of the Sensor 403

In the following, regarding the structure of the sensor 403 of the embodiment, description is made with reference to FIGS. 19 and 20. As shown in FIG. 17, the sensor 403 of the embodiment is formed in a rectangular shape when viewed from the top. However, an arbitrary shape can be selected as appropriate for the shape of the sensor 403. The sensor 403 includes multiple (four in the embodiment) detection regions 404. The detection region 404 detects the seated state of the seated person or the biological information of the seated person. However, the number of the detected regions 404 is not limited to four, and may also be two, three, or five or more.

The detection region 404 of the embodiment is formed in a rectangular shape when viewed from the top. However, the shape of the detection region 404 is not limited to being rectangular. An arbitrary shape, such as a polygonal shape like a triangular shape or a pentagonal shape, can be selected as appropriate. The four detection regions 404 are disposed to be spaced apart from each other at intervals at the four corners of the sensor 403 formed in a rectangular shape.

In the sensor 403, a conductive pattern (not shown) is formed in a region among the detection regions 404. With the conductive pattern, the detection regions 404 and the outside of the sensor 403 are electrically connected.

As shown in FIG. 17, the four detection regions 404 are a left-rear detection region 404a disposed at the left-rear part of the sensor 403 to detect the state of the left buttock of the seated person, a right-rear detection region 404b disposed at the right-rear part of the sensor 403 to detect the state of the right buttock of the seated person, a left-front detection region 404c disposed at the left-front part of the sensor 403 to detect the state of the left leg of the seated person, and a right-front detection region 404d disposed at the right-front part of the sensor 403 to detect the state of the right leg of the seated person. In the following description, regarding the common configuration of the four detection regions 404, the description may be made with the expression "detection region 404" without distinguishing the four detection regions 404.

The sensor 403 includes a rear ventilation through hole 405a between the left-rear detection region 404a and the right-rear detection region 404b. The sensor 403 includes a left ventilation through hole 405b between the left-front detection region 404c and the left-rear detection region 404a. The sensor 403 includes a right ventilation through hole 405c between the right-front detection region 404d and the right-rear detection region 404b.

As shown in FIG. 19, the rear ventilation through hole 405a is disposed at a position overlapped with the skin through hole 470 in the stacking direction.

Meanwhile, the left ventilation through hole 405b and the right ventilation through hole 405c are disposed at positions not overlapped with the skin through holes 470 in the stacking direction and are disposed in the vicinities of the skin through holes 470.

It is noted that the conductive pattern is formed to avoid portions where the rear ventilation through hole 405a, the left ventilation through hole 405b, and the right ventilation through hole 405c are formed.

Figure 20:
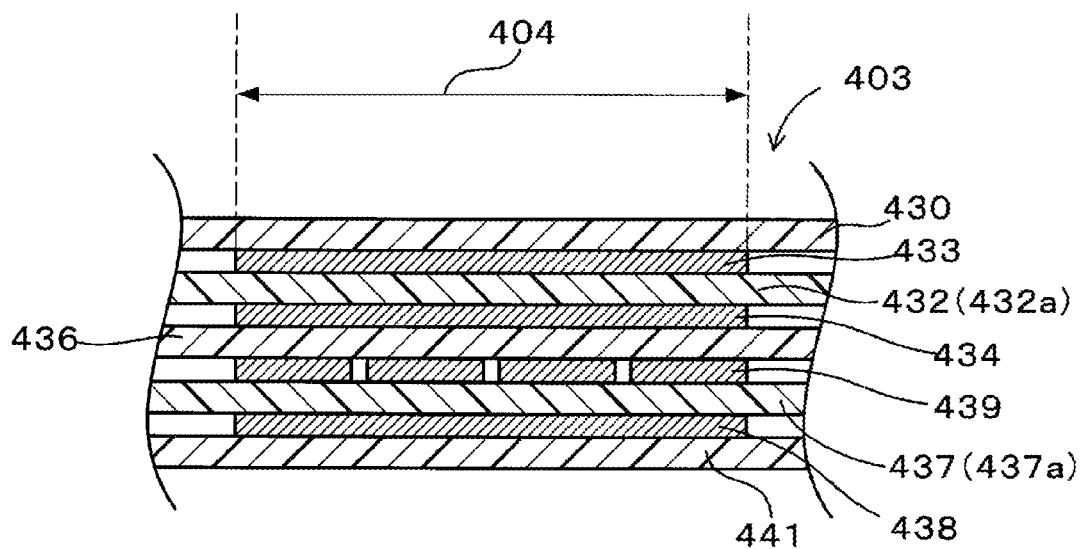
FIG. 20 is a cross-sectional view illustrating a detection region of the sensor forming the sensor-equipped seat according to Embodiment 9.

FIG. 20 illustrates the cross-sectional structure of one detection region. In the embodiment, the four detection regions 404 have the same configuration. In the detection region 404, a second film sheet 441 that is insulating, a second electrode sheet 437, an insulating sheet 436 that is insulating, a first electrode sheet 432, and a first film sheet 430 that is insulating are stacked.

The second electrode sheet 437 has a second body part 437a that is insulating. On the surface on the side of the second film sheet 441 in the second body part 437a, a second shield layer 438 that is conductive is stacked. On the surface on the side of the insulator sheet 436 in the second body part 437a, a second electrode layer 439 that is conductive is stacked. The second electrode layer 439 is formed by multiple electrode groups.

The first electrode sheet 432 has a first body part 432a that is insulating. On the surface on the side of the first film sheet 430 in the first body part 432a, a first shield layer 433 that is conductive is stacked. On the surface on the side of the insulator sheet 436 in the first body part 432a, a first electrode layer 434 that is conductive is stacked. The first electrode layer 434 is formed by one electrode.

However, the configuration of the detection region 404 is not limited to the above, and an arbitrary configuration can be selected as appropriate.

9-3. Suspension Structure of the Seating Surface Skin Member 413

In the following, regarding the suspension structure of the seating surface skin member 413, the description is made with reference to FIGS. 17, 18, 19, 21. As shown in FIG. 19, on the upper surface of the seating surface skin member 413, at portions near two side parts in the left-right direction, the two side suspension grooves 471a extending in the front-rear direction are formed. The side suspension groove 471a is formed to extend from the rear end until the front end of the seating surface skin member 413. In the side suspension groove 471a, the end of the seating surface skin member 413 is folded into the side of the first seating surface seat cushion 412.

Figure 21:
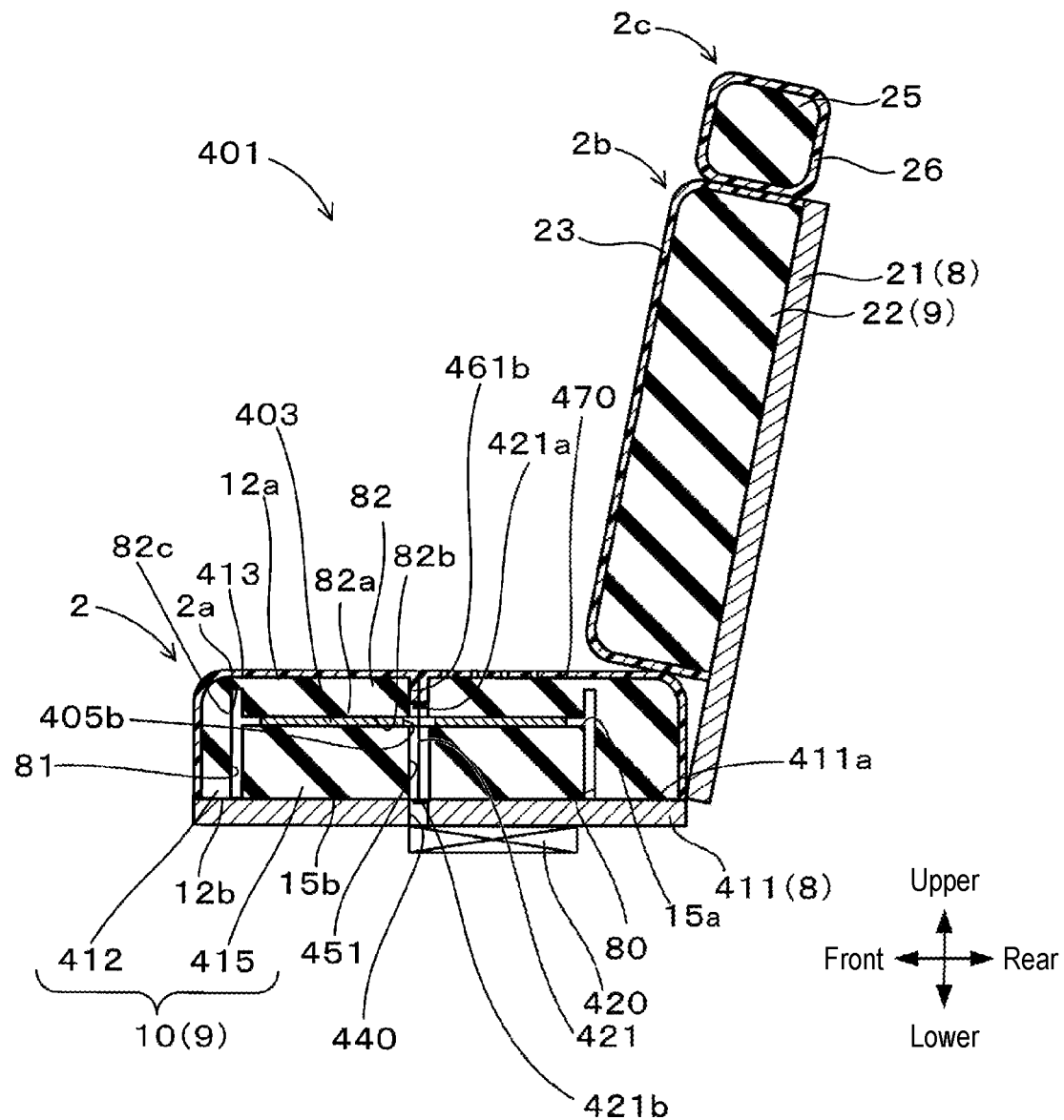
FIG. 21 is a cross-sectional view of the sensor-equipped seat of Embodiment 9, and is a cross-sectional view taken along a line XXI-XXI of FIG. 19.

As shown in FIG. 19, on the upper surface of the seating surface skin member 413, a central suspension groove 471b is formed. The central suspension groove 471b is near the substantial center in the front-rear direction and links the two side suspension grooves 471a. As shown in FIG. 21, in the central suspension groove 471b, the end of the seating surface skin member 413 is folded into the side of the first seating surface seat cushion 412.

As shown in FIG. 18, two side accommodation grooves 462a and a central accommodation groove 462b for accommodating the folded ends of the seating surface skin member 413 are formed on the upper surface of the first seating surface seat cushion 412 at positions corresponding to the two side suspension grooves 471a and the central suspension groove 471b.

In each of the two side accommodation grooves 462a, two first suspension through holes 461a spaced apart at an interval in the front-rear direction and suspending the ends of the seating surface skin member 413 are formed to penetrate through the first seating surface cushion in the stacking direction (upper-lower direction). The first suspension through hole 461a formed in the side accommodation groove 462a is formed in an elongated oval shape thin and long in the front-rear direction. The number of first suspension through holes 461a formed in the side accommodation groove 462a may also be one or three or more.

In the central accommodation groove 462b, two first suspension through holes 461b spaced apart at an interval in the left-right direction and suspending the ends of the seating surface skin member 413 are formed to penetrate through the first seating surface cushion in the stacking direction (upper-lower direction). The first suspension through hole 461b formed in the central accommodation groove 462b is formed in an elongated oval shape thin and long in the left-right direction. The number of first suspension through holes 461b formed in the central accommodation groove 462b may also be one or three or more.

However, the shapes of the first suspension through holes 461a, 461b are not limited to the long hole shape, and an arbitrary shape, such as a circular shape, an elongated rectangular shape, etc., can be selected as appropriate.

As shown in FIG. 21, in the first suspension through hole 461b, the end of the surface skin member 413 is inserted from the top.

As shown in FIG. 18, the first suspension through holes 461b formed in the central accommodation groove 462b are formed at positions overlapped with the left ventilation through hole 405b and the right ventilation through hole 405c of the sensor 403 when projected in the stacking direction.

As shown in FIG. 21, in the second seating surface seat cushion 415, a second suspension through hole 451 for suspending the skin is formed to penetrate through the second seating surface cushion in the stacking direction (upper-lower direction) at a position overlapped with the first suspension through hole 461b when projected in the stacking direction. A support member 421 to be described afterwards is inserted into the second suspension through hole 451.

As shown in FIG. 17, the second suspension through hole 451 is formed in a long hole shape thin and long in the left-right direction. However, the shape of the second suspension through hole 451 is not limited to the long hole shape, and an arbitrary shape, such as a circular shape, an elongated rectangular shape, etc., can be selected as appropriate.

As shown in FIG. 21, the seating surface seat frame 411 has the frame through hole 440 penetrating through the seating surface seat frame 411 in the stacking direction at a position overlapped with the second suspension through hole 451 when projected in the stacking direction. By using the ventilation device 420, the air is configured to be able to circulate in the frame through hole 440.

With reference to FIG. 21, the suspension structure of the seating surface skin member 413 is described. A skin side locking member 421a is fixed to an end of the seating surface skin member 413 folded into the first suspension through hole 461b of the first seating surface seat cushion 412. The skin side locking member 421a fixes the end of the seating surface skin member 413 and one end of the support member 421. The shape of the skin side locking member 421a is not particularly limited, and any arbitrary shape, such as a ring shape, a hook shape, can be selected.

The support member 421 is formed in an elongated shape in the stacking direction. The support member 421 may be a metal rod member, a metal plate member, a metal wire, a synthetic resin member, a synthetic resin wire, etc., and is not particularly limited. In the embodiment, a metal wire is used as the support member 421.

As shown in FIG. 21, the support member 421 is inserted into the ventilation through hole 405 of the sensor 403 and the second suspension through hole 451 of the second seating surface seat cushion 415. A frame side locking member 421b is fixed to the other end of the support member 421. The shape of the frame side locking member 421b is not particularly limited, and any arbitrary shape, such as a ring shape, a hook shape, can be selected. The frame side locking member 421b is inserted into the frame through hole 440 of the seating surface seat frame 411, and is fixed to the seating surface seat frame 411 in the frame through hole 440.

9-4. Effects of the Embodiment

The sensor 403 of the embodiment has the ventilation through hole 405. Accordingly, even in the case where the sensor 403 is disposed between the first seating surface seat cushion 412 and the second seating surface seat cushion 415, air can flow between the first seating surface seat cushion 412 and the second seating surface seat cushion 415 via the ventilation through hole 405. As a result, by using the ventilation device 420, the air can be blown to the buttocks of the seated person through the frame through hole 440, the second ventilation passage 450, the ventilation through hole 405, the first ventilation passage 460, and the skin through hole 470. Accordingly, the stuffiness due to the sweat of the seated person between the buttocks of the seated person and the seating surface skin member 413 can be suppressed.

According to the embodiment, with the support member 421 installed to the end of the seating surface skin member 413 being inserted into the ventilation through hole 405 formed in the sensor 403, the support member 421 can be fixed to the seating surface seat frame 411. Accordingly, even in the case where the sensor 403 is disposed between the first seating surface seat cushion 412 and the second seating surface seat cushion 415, the end of the seating surface skin member 413 can be suspended in the first seating surface seat cushion 412. Accordingly, the position deviation of the seating surface skin member 413 is suppressed, and the designability of the seating surface skin member 413 can be facilitated.

In addition, since the seating surface skin member 413 is fixed in a state of being suspended from the seating surface seat frame 411 via the support member 421, the seating surface skin member 413 is in a state of being pulled toward the first seating surface seat cushion 412 and the second seating surface seat cushion 415. Accordingly, pre-compression is applied to the sensor 403 sandwiched by the first seating surface seat cushion 412 and the second seating surface seat cushion 415. As a result, the sensitivity of the sensor 403 can be increased.

In addition, the ventilation through hole 405 of the sensor 403 is formed at a position overlapped with the first suspension through hole 461b of the first seating surface seat cushion 412 and the second suspension through hole 451 of the second seating surface seat cushion 415 when projected in the stacking direction. Therefore, by using the ventilation device 420, air can flow from the side of the second seating surface seat cushion 415 to the side of the first seating surface seat cushion 412. Accordingly, the stuffiness between the buttocks of the seated person and the seating surface skin member 413 can be suppressed.

In addition, according to the embodiment, the ventilation through hole 405 can have the function of causing air to flow as well as the function of inserting the support member 421, and the number of through holes provided in the sensor 403 can be reduced. Accordingly, the degree of freedom for designing the conductive pattern formed in the sensor 403 can be increased.

Embodiment 10

Figure 22:
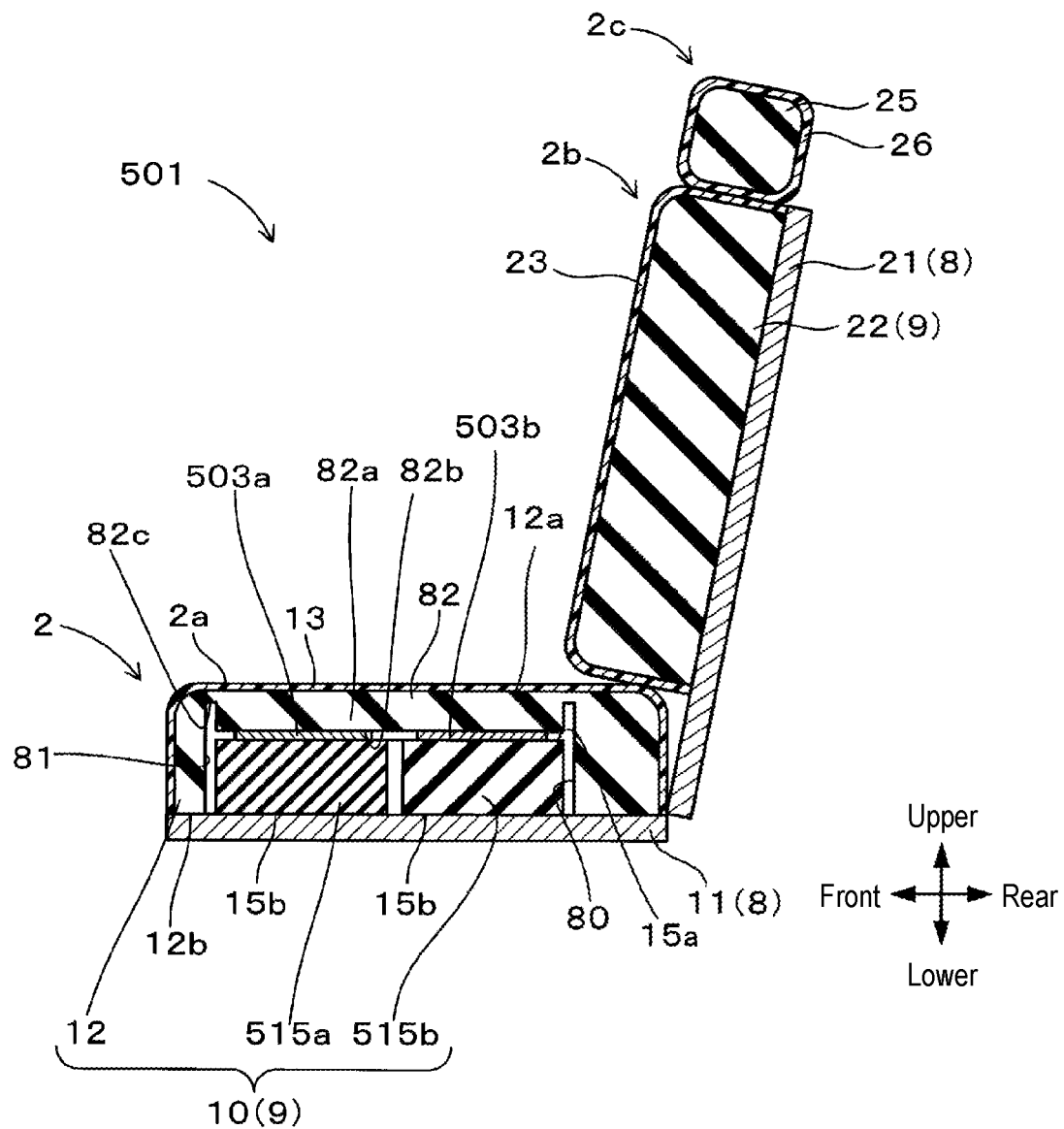
FIG. 22 is a cross-sectional view illustrating a sensor-equipped seat according to Embodiment 10.

Next, a sensor-equipped seat 501 of Embodiment 9 is described with reference to FIG. 22. The sensor-equipped seat 501 of the embodiment has a front sensor 503a disposed on the front side and a rear sensor 503b disposed on the rear side. The front sensor 503a and the rear sensor 503b are disposed at an interval in the front-rear direction. However, the number of sensors is not limited to 2, and may be three or more.

A front second seating surface seat cushion 515a (an example of second cushion) is disposed below the front sensor 503a. In addition, a rear second seating surface seat cushion 515b (an example of second cushion) is disposed below the rear sensor 503b. However, it suffices as long as the second cushion is disposed at a position below the sensor. Therefore, the number of the second cushions is not limited to 2, but may also be 3 or more.

The elastic modulus of the front second seating surface seat cushion 515a may be the same as or different from the elastic modulus of the rear second seating surface seat cushion 515b. By making the elastic modulus of the front second seating surface seat cushion different from the rear second seating surface seat cushion 515b, the pre-compression applied to the front sensor 503a and the pre-compression applied to the rear sensor 503b can be different. Accordingly, the sensitivities of the front sensor 503a and the rear sensor 503b can be regulated.

The material of the front second seating surface seat cushion 515a and the material of the rear seating surface seat cushion may be the same or different. In the case where the material of the front second seating surface seat cushion 515a and the material of the second seating surface seat cushion 515b are the same, for example, the elastic moduli can be different by making foam rates different.

The disclosure is not limited to the above-mentioned embodiments, but can be applied to various embodiments without departing from the gist thereof.

What is claimed is:
1. A sensor-equipped seat (1), comprising:
an installation member (11), having an installation seating surface (11a);
a seat cushion (10), which is a seat cushion installed to the installation seating surface of the installation member and has: a first cushion (12) having an accommodation concave part (80) open to a side of the installation member in a counter pressure-receiving surface (12b) located on a back side of a pressure-receiving surface (12a) receiving a pressure from a seated person; and a second cushion (15), accommodated in the accommodation concave part of the first cushion to be stacked on the first cushion; and a sensor (3), disposed between a first pressing surface (82b) located on a side opposite to a direction in which the accommodation concave part is open in the accommodation concave part of the first cushion and a second pressing surface (15a) located on a side opposite to the installation member in the second cushion, detecting a seated state of the seated person or biological information of the seated person by detecting a physical quantity in accordance with a pressure transmitted from the pressure-receiving surface of the seat cushion via the first cushion in the seated state by the seated person, and having a flexible property, wherein the seat cushion is installed to the installation seating surface of the installation member and, in an unseated state prior to the seated person being seated at the seat cushion, the first cushion and the second cushion are pre-compressed in a stacking direction in which the first cushion and the second cushion are stacked, and the sensor is applied with pre-compression by a compression reaction force of the first cushion and the second cushion.

2. The sensor-equipped seat as claimed in claim 1, wherein an elastic modulus of the second cushion is different from an elastic modulus of the first cushion.

3. The sensor-equipped seat as claimed in claim 1, wherein in a state before the seat cushion is installed to the installation member, a sum (b) of a thickness dimension of the second cushion and a thickness dimension of the sensor in the stacking direction is set to be greater than a depth dimension (a) of the accommodation concave part of the first cushion in the stacking direction.

4. The sensor-equipped seat as claimed in claim 3, wherein, in the unseated state, the counter pressure-receiving surface of the first cushion and a surface (15b) facing the installation seating surface in the second cushion are flush.

5. The sensor-equipped seat as claimed in claim 1, wherein the installation member comprises:

a pressing convex part (111b) protruding toward the second cushion at a position corresponding to the second cushion in the installation seating surface.

6. The sensor-equipped seat as claimed in claim 1, wherein a gap is formed between an inner side surface of the accommodation concave part of the first cushion and an outer side surface of the second cushion.

7. The sensor-equipped seat as claimed in claim 1, wherein the sensor comprises:

a pressure detection surface (31), located on a side opposite to the second cushion in a state arranged between the first pressing surface of the first cushion and the second pressing surface of the second cushion, and directly or indirectly receiving a pressure from the first pressing surface of the first cushion, and the first cushion comprises:

a convex part (82a), protruding from a bottom part (82) of the accommodation concave part toward the sensor and contacting the pressure detection surface to be pre-compressed in the unseated state, wherein a tip end of the convex part is arranged as the first pressing surface, and a pre-compression amount with respect to the pressure detection surface is set to be greater than a pre-compression amount with respect to a periphery of the pressure detection surface.

8. The sensor-equipped seat as claimed in claim 7, wherein the first cushion further comprises:

a recessed groove (82c), formed at the bottom part of the accommodation concave part and along an edge of the convex part, and separating an outer side surface of the convex part and an inner side surface of the accommodation concave part.

9. The sensor-equipped seat as claimed in claim 1, comprising an elastic layer (90) between the first cushion and the sensor or between the second cushion and the sensor, the elastic layer being elastically deformable.

10. The sensor-equipped seat as claimed in claim 9, wherein in a state before the seat cushion is installed to the installation member, a sum (b) of a thickness dimension of the second cushion, a thickness dimension of the sensor, and a thickness dimension of the elastic layer in the stacking direction is set to be greater than a depth dimension (a) of the accommodation concave part of the first cushion in the stacking direction.

11. The sensor-equipped seat as claimed in claim 9, wherein the elastic layer is arranged between the first cushion and the sensor, the sensor comprises: a pressure detection surface (31), in a state arranged between the first pressing surface of the first cushion and the second pressing surface of the second cushion, located on a side opposite to the second cushion, and directly or indirectly receiving a pressure from the first pressing surface of the first cushion, the elastic layer contacts the pressure detection surface, an area of the elastic layer is equal to or less than an area of the pressure detection surface, and, in the unseated state, a pre-compression amount with respect to the pressure detection surface is set to be greater than a pre-compression amount with respect to a periphery of the pressure detection surface.

12. The sensor-equipped seat as claimed in claim 1, wherein the first cushion is covered by a skin (13) formed by a material less contractible than the first cushion.

13. The sensor-equipped seat as claimed in claim 1, wherein the sensor comprises:

an insulator sheet (36), having an insulation property, and provided with a first surface (36a) and a second surface (36b);

a first electrode sheet (32), stacked on the first surface of the insulator sheet and having a first electrode layer (34);

a first film sheet (30), having an insulation property and covering the first electrode sheet;

a second electrode sheet (37), stacked on the second surface of the insulator sheet and having a second electrode layer (39); and a second film sheet (41), having an insulation property and covering the second electrode sheet, wherein in a state in which the sensor is arranged in the accommodation concave part, the first film sheet is arranged in a vicinity of the first pressing surface and the second film sheet is arranged in a vicinity of the second pressing surface, and the sensor comprises a sensor elastic layer (91) that is elastically deformable.

14. The sensor-equipped seat as claimed in claim 13, wherein the sensor elastic layer is arranged at at least one of between the first electrode sheet and the first film sheet and between the second electrode sheet and the second film sheet.

15. The sensor-equipped seat as claimed in claim 13, wherein the sensor elastic layer is the insulator sheet.

16. The sensor-equipped seat as claimed in claim 13, wherein the first electrode sheet comprises:
a first body part (32a) that has an insulation property;
the first electrode layer, stacked on a surface facing the first surface of the insulator sheet in the first body part; and
a first shield layer (33), in the first body part, stacked on a surface on a side opposite to the first electrode layer, and
the second electrode sheet comprises:
a second body part (37a) that has an insulation property;
the second electrode layer, in the second body part, stacked on a surface facing the second surface of the insulator sheet; and
a second shield layer (38), stacked on a surface on a side opposite to the second electrode layer in the second body part.

17. The sensor-equipped seat as claimed in claim 1, wherein the sensor-equipped seat further comprises:
a ventilation device (420), causing air to flow with respect to the first cushion and the second cushion in the stacking direction, wherein
the first cushion comprises:
a first ventilation passage (460) penetrating through the first cushion in the stacking direction,
the second cushion comprises:
a second ventilation passage (450) penetrating through the second cushion in the stacking direction,
the first ventilation passage and the second ventilation passage are formed at positions overlapped in the stacking direction, and
the sensor has a ventilation through hole (405a) at a position overlapped with the first ventilation passage and the second ventilation passage when projected in the stacking direction, the ventilation through hole penetrating through the sensor.

18. The sensor-equipped seat as claimed in claim 17, wherein the sensor has a plurality of detection regions (404, 404a, 404b, 404c, 404d) detecting the seated state of the seated person or biological information of the seated person, and
the detection regions are disposed to be spaced apart from each other at intervals, and
the ventilation through hole is formed between adjacent detection regions among the detection regions.

19. The sensor-equipped seat as claimed in claim 17, wherein the first cushion is covered by a skin (413) formed by a material less contractible than the first cushion,
in the first cushion, a first suspension through hole (461b) for suspending the skin is formed by penetrating in the stacking direction,
in the second cushion, a second suspension through hole (451) for suspending the skin is formed by penetrating in the stacking direction at a position overlapped with the first suspension through hole when projected in the stacking direction,
a support member (421) supporting the skin that is suspended is disposed inside the first suspension through hole and the second suspension through hole, and
ventilation holes (405b, 405c) are formed at positions overlapped with the first suspension through hole and the second suspension through hole when projected in the stacking direction.

20. The sensor-equipped seat as claimed in claim 19, wherein the support member is formed in an elongated shape in the stacking direction, an end of the support member is fixed to the skin, and an other end of the support member is fixed to the installation member, and
with the skin being pulled by the support member toward the installation member, the first cushion and the second cushion are pre-compressed in the stacking direction.

21. The sensor-equipped seat as claimed in claim 1, wherein the sensor-equipped seat further comprises:
a plurality of sensors (503a, 503b); and
a plurality of second cushions (515a, 515b) disposed at positions overlapped with the sensors in the stacking direction.

22. The sensor-equipped seat as claimed in claim 21, wherein an elastic modulus at least one of the second cushions is different from an elastic modulus of an other one of the second cushions.

* * * * *